United States Patent
Jarvik et al.

(10) Patent No.: US 6,716,189 B1
(45) Date of Patent: Apr. 6, 2004

(54) CIRCULATORY SUPPORT SYSTEM

(75) Inventors: Robert Jarvik, New York, NY (US);
Daniel E. Alesi, Sherman, CT (US);
John F. Klinger, Danbury, CT (US);
Robert J. Geiste, Milford, CT (US);
Steven R. Day, Mukilteo, WA (US);
Keith Payea, Kirkland, WA (US);
Kenneth G. Hammerquist, Kirkland,
WA (US); Steven J. Stern, Issaquah,
WA (US); Francis X. Kaczynski,
Bellevue, WA (US); Mark Howansky,
Wilton, CT (US); Deborah M. Cashin,
Norwalk, CT (US)

(73) Assignee: United States Surgical Corporation,
Norwalk, CT (US)

( * ) Notice: Subject to any disclaimer, the term of this patent is extended or adjusted under 35 U.S.C. 154(b) by 0 days.

(21) Appl. No.: 09/328,248

(22) Filed: Jun. 8, 1999

Related U.S. Application Data

(62) Division of application No. 08/943,504, filed on Oct. 3, 1997, now Pat. No. 5,965,089.
(60) Provisional application No. 60/028,070, filed on Oct. 4, 1996, provisional application No. 60/026,656, filed on Oct. 4, 1996, and provisional application No. 60/026,657, filed on Oct. 4, 1996.

(51) Int. Cl.[7] .................. A61M 37/00; A61M 31/00
(52) U.S. Cl. ............... 604/6.16; 604/4.01; 604/6.11; 604/65; 604/67
(58) Field of Search .................. 604/65–67, 799, 604/4.01, 6.11, 6.14, 6.16, 28, 30, 31, 43, 506–509, 96.01; 422/44

(56) References Cited

U.S. PATENT DOCUMENTS 2,635,547 A   4/1953   Cataldo
3,608,088 A   9/1971   Dorman et al.
3,647,324 A   3/1972   Rafferty et al.
3,685,059 A   8/1972   Bokros et al.
3,935,876 A   2/1976   Massie et al.
RE28,742 E   3/1976   Rafferty et al.
3,957,389 A   5/1976   Rafferty et al.
3,995,617 A   12/1976  Watkins et al.
4,037,984 A   7/1977   Rafferty et al.

(List continued on next page.)

FOREIGN PATENT DOCUMENTS

DE   3720667   1/1989
FR   1503906   10/1967
FR   1514319   1/1968
WO   9601416   3/1986
WO   9618358   6/1996

Primary Examiner—Angela D. Sykes
Assistant Examiner—Leslie R. Deak

(57) ABSTRACT

A method for providing at least partial bypass of the heart to supplement the pumping function of the heart to thereby enable the surgeon to perform various surgical procedures thereon includes providing a circulatory assist system having a portable extracorporeal axial flow pump with a pump housing, a rotating pumping member disposed in the pump housing and inlet and outlet cannulated tubes respectively connected to inlet and outlet ports of the pump housing, accessing the patient's left atrium of the heart with the inlet cannulated tube, accessing the aorta with the outlet cannulated tube, actuating the rotating pumping member to draw oxygenated blood from the left atrium of the heart through the lumen of the inlet cannulated tube and into the inlet port of the pump housing whereby the pumping member imparts mechanical energy to the oxygenated blood passing through the pump housing and directs the oxygenated blood through the outlet port and through the lumen of the outlet cannulated tube to be transferred by the aorta to the systemic arteries and permitting the right side of the heart to function whereby oxygen-depleted blood returning through the systemic veins to the right atrium is directed through the right ventricle to the patient's lungs for oxygenation and subsequent pulmonary circulation.

11 Claims, 25 Drawing Sheets

U.S. PATENT DOCUMENTS

| | | | |
|---|---|---|---|
| 4,068,521 A | 1/1978 | Cosentino et al. | |
| 4,135,253 A | 1/1979 | Reich et al. | |
| 4,173,796 A | 11/1979 | Jarvik | |
| 4,280,495 A | 7/1981 | Lampert | |
| 4,382,199 A | 5/1983 | Isaacson | |
| 4,507,048 A | 3/1985 | Belenger et al. | |
| 4,589,822 A | 5/1986 | Clausen et al. | |
| 4,625,712 A | 12/1986 | Wampler | |
| 4,657,529 A * | 4/1987 | Prince et al. | 128/DIG. 13 |
| 4,662,355 A | 5/1987 | Pieronne et al. | |
| 4,688,998 A | 8/1987 | Olsen et al. | |
| 4,704,121 A | 11/1987 | Moise | |
| 4,747,826 A * | 5/1988 | Sassano | 604/52 |
| 4,753,221 A | 6/1988 | Kensey et al. | |
| 4,763,032 A | 8/1988 | Bramm et al. | |
| 4,779,614 A | 10/1988 | Moise | |
| 4,795,314 A * | 1/1989 | Prybella et al. | 417/43 |
| 4,817,586 A | 4/1989 | Wampler | |
| 4,846,152 A | 7/1989 | Wampler et al. | |
| 4,895,493 A | 1/1990 | Kletschka | |
| 4,898,518 A | 2/1990 | Hubbard et al. | |
| 4,906,229 A | 3/1990 | Wampler | |
| 4,908,012 A | 3/1990 | Moise et al. | |
| 4,922,910 A * | 5/1990 | Kanai et al. | 128/642 |
| 4,927,407 A | 5/1990 | Dorman | |
| 4,944,722 A | 7/1990 | Carriker et al. | |
| 4,955,856 A | 9/1990 | Phillips | |
| 4,957,504 A | 9/1990 | Chardack | |
| 4,964,864 A | 10/1990 | Summers et al. | |
| 4,969,865 A | 11/1990 | Hwang et al. | |
| 4,984,972 A | 1/1991 | Clausen et al. | |
| 4,994,078 A | 2/1991 | Jarvik | |
| 4,995,857 A | 2/1991 | Arnold | |
| 5,011,469 A | 4/1991 | Buckberg et al. | |
| 5,049,134 A | 9/1991 | Golding | |
| 5,055,005 A | 10/1991 | Kletschka | |
| 5,092,836 A * | 3/1992 | Polaschegg | 604/4 |
| 5,092,879 A | 3/1992 | Jarvik | |
| 5,112,292 A | 5/1992 | Hwang et al. | |
| 5,118,264 A | 6/1992 | Smith | |
| 5,145,333 A | 9/1992 | Smith | |
| 5,147,388 A | 9/1992 | Yamazaki | |
| 5,242,384 A * | 9/1993 | Robinson et al. | 604/4 |
| 5,376,114 A | 12/1994 | Jarvik | |
| 5,391,142 A * | 2/1995 | Sites et al. | 604/4 |
| 5,613,935 A | 3/1997 | Jarvik | |
| 5,662,711 A * | 9/1997 | Douglas | 623/12 |
| 5,711,753 A | 1/1998 | Pacella et al. | |
| 5,713,865 A | 2/1998 | Manning et al. | |
| 5,755,784 A | 5/1998 | Jarvik | |
| 5,776,190 A | 7/1998 | Jarvik | |
| 5,851,174 A | 12/1998 | Jarvik et al. | |
| 5,888,241 A | 3/1999 | Jarvik | |
| 5,965,089 A | 10/1999 | Jarvik | |
| 6,083,187 A * | 7/2000 | Nakayama et al. | 604/6 |

* cited by examiner

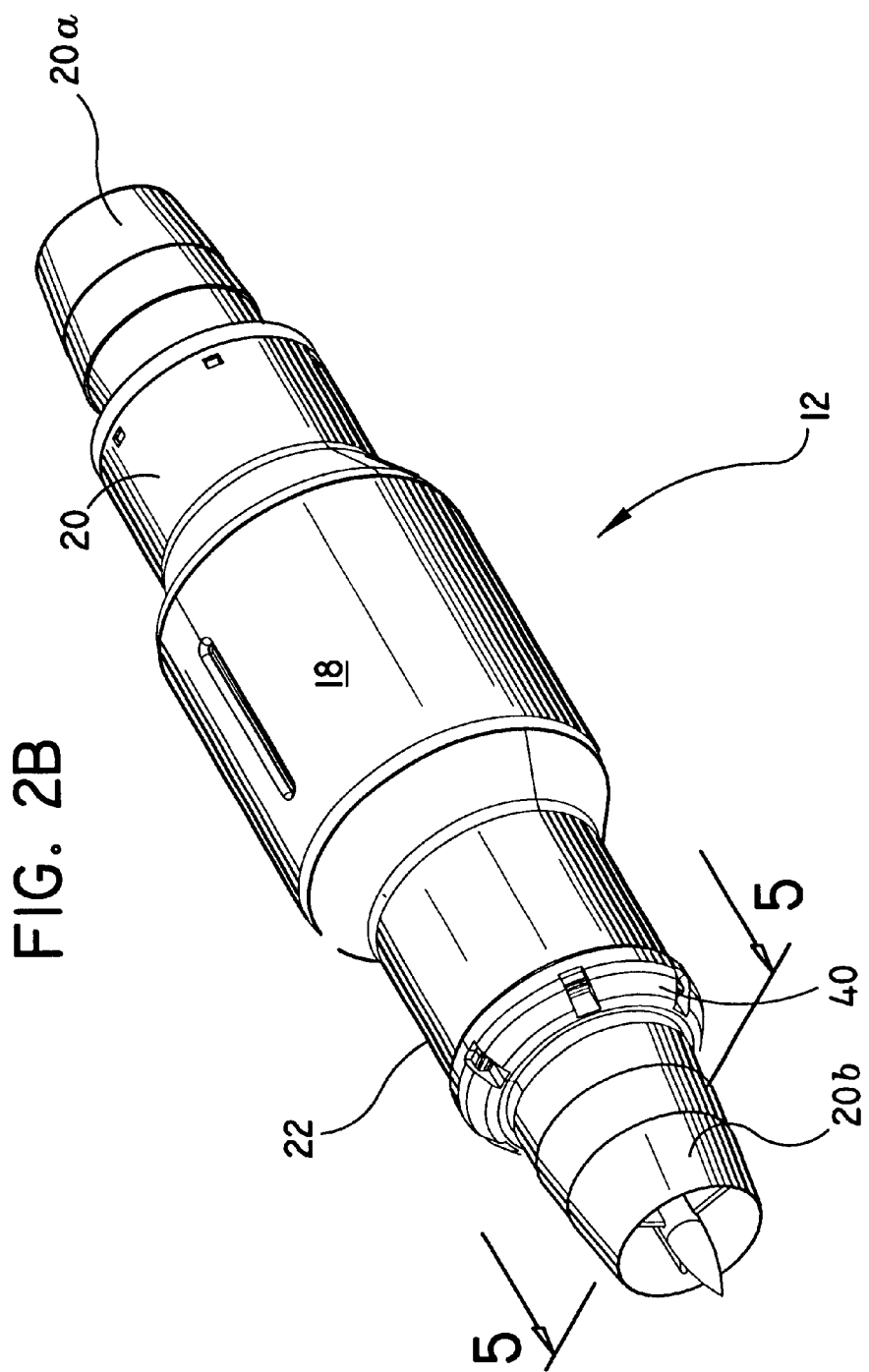

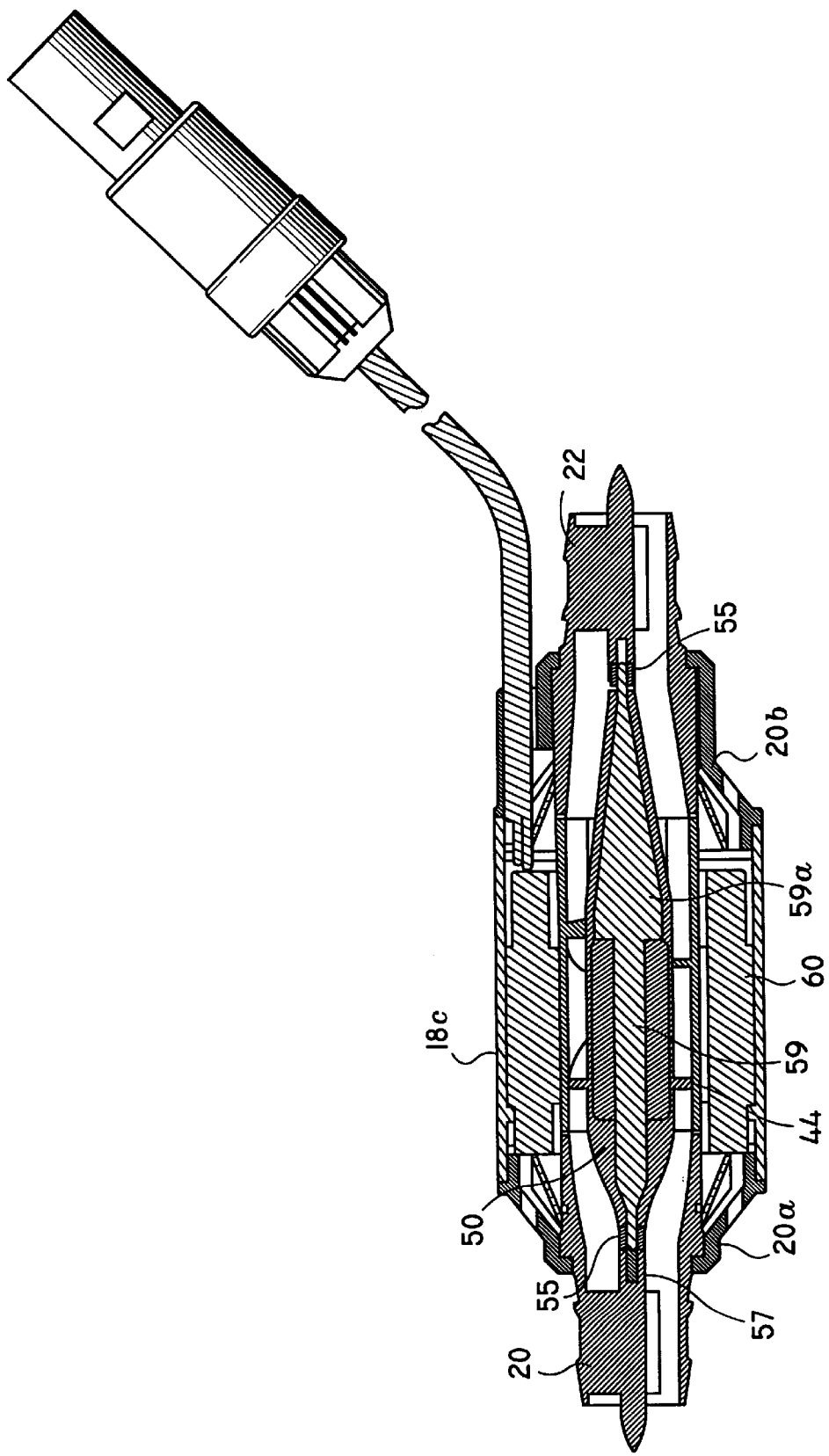

CIRCULATORY SUPPORT SYSTEM

CROSS-REFERENCE TO RELATED APPLICATIONS

This application is a divisional application of U.S. application Ser. No. 08/943,504, filed Oct. 3, 1997, now U.S. Pat. No. 5,965,089, which claims priority to U.S. Provisional Application Nos. 60/028,070, 60/026,656 and 60/026,657, each filed Oct. 4, 1996.

BACKGROUND

1. Technical Field

The present disclosure relates generally to circulatory support systems, and, more particularly, to a circulatory support system to provide partial or total bypass of the heart. The present disclosure is further directed to an axial flow pump and a portable microprocessor-based controller each being adapted for use in the circulatory support system.

2. Background of the Related Art

Mechanical blood pumps are commonly utilized to temporarily support or substitute the pumping function of the heart during heart surgery or during periods of heart failure. The most widely applied blood pumps include roller pumps and centrifugal pumps. Typically, these pumps are a component of a cardiopulmonary bypass system (e.g., a heart-lung machine) which includes an oxygenator, a heat exchanger, blood reservoirs and filters, and tubing which transports the blood from the patient through the bypass system and back to the patient. With these systems, blood is withdrawn from the patient via uptake cannula positioned within the vena cavae and atria or ventricles of the heart and pumped back into the pulmonary artery and aorta via a return cannula.

Although the aforedescribed cardiopulmonary bypass systems have been generally effective for their intended purposes, these systems are subject to certain disadvantages which detract from their usefulness. In particular, conventional bypass systems are relatively complicated and expensive to manufacture, expose the blood to a high surface area of foreign materials which may damage the blood, require full anticoagulation and cooling of the heart, and require considerable set up time and continual management by a skilled technician. These systems also require mechanical oxygenation of the blood which can have adverse affects on the patient.

U.S. Pat. No. 4,610,656 to Mortensen/Mehealus Partnership discloses a semi-automatic heart-lung substitution system. The Mortensen '656 system includes a roller pump which pumps blood from the patient's right heart via a venous cannula to a membrane oxygenator connected at the output of the roller pump. From the oxygenator, the blood flows to a compliance reservoir which is connected to a pulsatile left heart pump. Blood is pumped by the pulsatile left heart pump through a filter and bubble trap and then returned to the patient's arterial system through an arterial cannula. The Mortensen '656 system, however, is also a relatively complex device including several pumps and an oxygenator and, consequently, requires attendance of skilled technicians for set-up and operation.

SUMMARY

Accordingly, the present disclosure is directed to a circulatory support system to support the functioning of the heart. In a preferred embodiment, the support system includes an extracorporeal pump member having a pump housing dimensioned for positioning directly on or adjacent to the chest area of a patient and defining inlet and outlet ports, a rotating member rotatably mounted in the pump housing to impart mechanical energy to blood entering the inlet port and to direct the blood through the outlet port, an inlet cannulated tube connected to the inlet port of the pump housing and having an inlet open end portion dimensioned for insertion within the patient's heart whereby blood is drawn from the heart through the inlet cannulated tube and directed into the pump housing, and an outlet cannulated tube connected to the outlet port of the pump housing and having an outlet end portion dimensioned for insertion within a major blood vessel associated with the heart whereby blood exiting the outlet port of the pump housing is conveyed through the outlet cannulated tube into the major blood vessel for transfer by the arterial system of the patient.

The support system is particularly contemplated for left heart bypass while the right heart functions to direct blood to the lungs. It is envisioned that the right heart may be slowed or even stopped while the support system is utilized for left heart bypass.

A method for providing at least partial bypass of the heart to supplement the pumping function of the heart to thereby enable the surgeon to perform various surgical procedures thereon is also disclosed. The method includes the steps of providing a circulatory assist system having a portable extracorporeal axial flow pump with a pump housing and inlet and outlet ports, a rotating pumping member disposed in the pump housing and inlet and outlet cannulated tubes respectively connected to the inlet and outlet ports of the pump housing, accessing the patient's left ventricle of the heart with the inlet cannulated tube, accessing the aorta with the outlet cannulated tube, actuating the rotating pumping member to draw oxygenated blood from the left ventricle of the heart through the lumen of the inlet cannulated tube and into the inlet port of the pump housing whereby the pumping member imparts mechanical energy to the oxygenated blood passing through the pump housing and directs the oxygenated blood through the outlet port and through the lumen of the outlet cannulated tube to be transferred by the aorta to the systemic arteries, and permitting blood returning through the systemic veins to the right atrium to be directed through the right ventricle to the patient's lungs for oxygenation and subsequent pulmonary circulation. The left ventricle may be accessed through the heart wall, mitral valve or aortic valve. In an alternate embodiment, a second circulatory assist system may be utilized to facilitate the pumping function of the right side of the heart.

The present disclosure is further directed to a pump to be used in the circulatory support system. The pump includes a pump housing including an inlet end portion defining an inlet port for permitting blood to enter the pump housing and an outlet end portion defining an outlet port for permitting blood to exit the pump housing. The inlet and outlet end portions preferably each have central hub portions with straightener blades extending therefrom for facilitating passage of blood through the pump housing. A rotatable member is mounted for rotational movement to the central hub portions of the pump housing. The rotatable member includes at least one impeller blade for imparting pump energy to blood passing through the pump housing and a magnetically actuated rotor. A motor stator is disposed in the pump housing and has at least one stator blade extending from an inner surface thereof. The one stator blade and the one impeller blade of the rotatable member are cooperatively configured to exert a substantially axial flow pumping energy to blood flowing along the blood path. Preferably, the one impeller blade and the one stator blade each extend axially and peripherally within the pump housing.

The present disclosure is further directed to a control unit to be used in the circulatory support system. In an exemplary embodiment, the control unit includes circuitry for supplying power to the flow pump to cause the pump to rotate, and circuitry responsive to a pressure sense signal from a pressure transducer located on the inlet side of the pump (e.g., within the atrium), for commanding a reduction in motor speed to a lower speed when the pressure is determined to be below a predetermined threshold. The control unit preferably also includes circuitry responsive to a bubble sense signal provided by a bubble detector mounted to one of the cannulas, for generating a bubble alarm and for causing rotation of the pump to cease if the bubble sense signal indicates the presence of an air bubble. The control unit may further include circuitry responsive to the bubble sense signal indicating the presence of an air bubble for causing a clamping device mounted to one of the cannulas to clamp down on the cannula to prevent air from entering the patient's bloodstream.

BRIEF DESCRIPTION OF THE DRAWINGS

Preferred embodiment(s) of the present disclosure are described herein with reference to the drawings wherein:

FIG. 2B is a perspective view of the portable pump;

FIG. 9A is a cross-sectional view of an alternate portable pump to be used with the circulatory support system of FIG. 1;

DETAILED DESCRIPTION OF PREFERRED EMBODIMENTS

Figure 1:
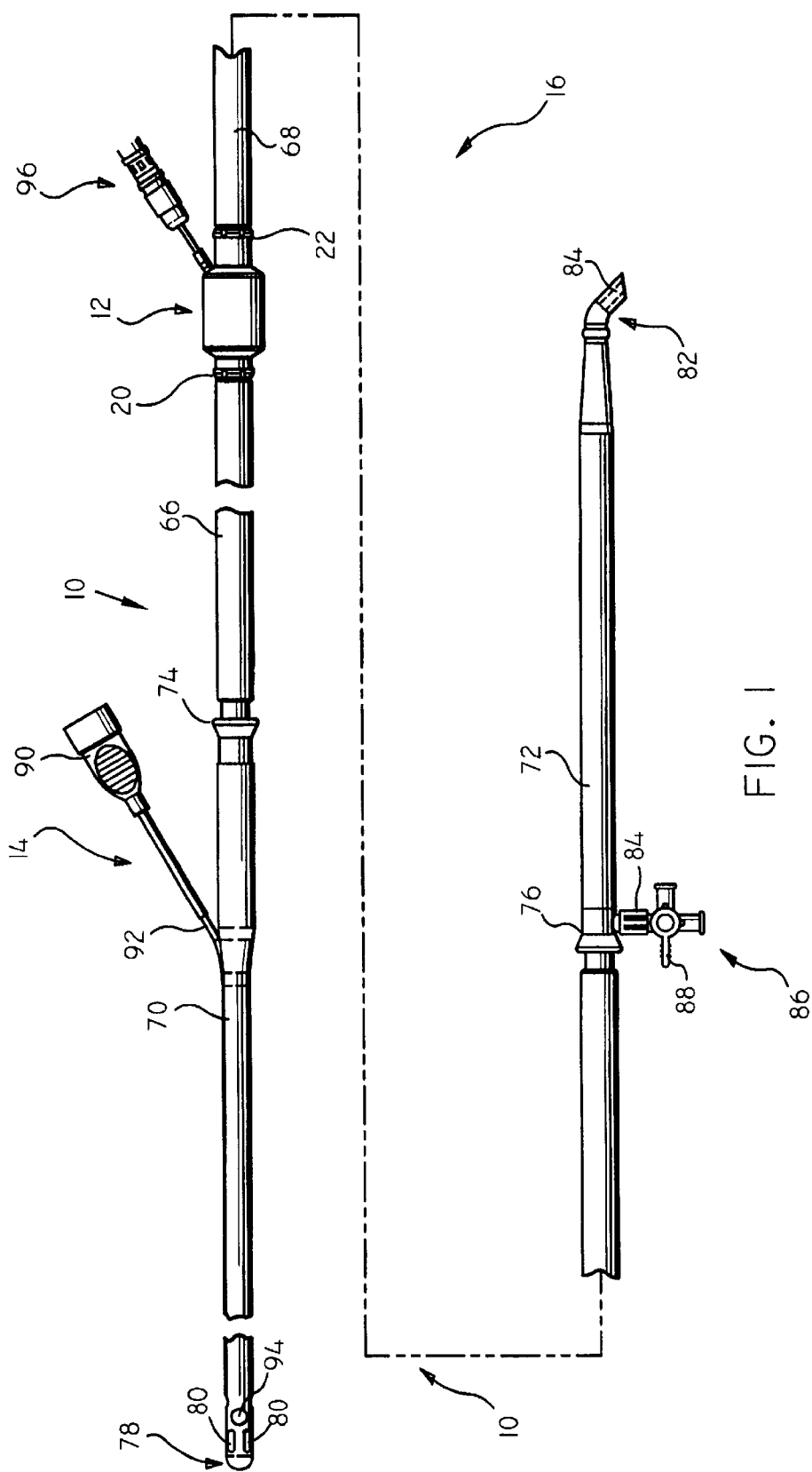
FIG. 1 is a side plan view of the circulatory support system of the present disclosure illustrating the portable pump and the pump inflow and outflow sections.
Figure 2A:
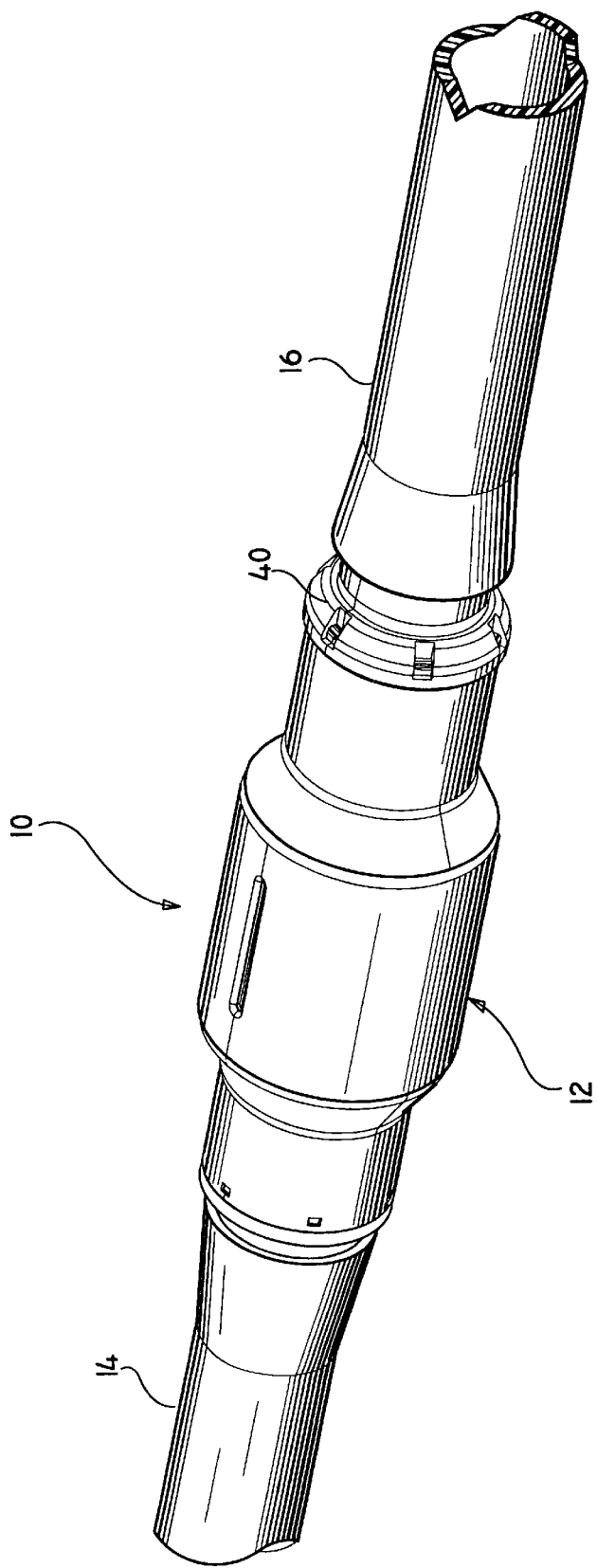
FIG. 2A is a perspective view of the portable pump of the circulatory support system with inflow and outflow sections.

Referring now in detail to the drawings where like reference numerals identify similar or like components throughout the several views, FIG. 1 illustrates a preferred embodiment of the circulatory support system in accordance with the principles of the present disclosure. Particular features of support system 10 are also disclosed in U.S. Provisional Application Nos. 60/028,070, 60/026,656 and 60/026,657, each filed Oct. 4, 1996, and each entitled CIRCULATORY SUPPORT SYSTEM, the contents of each being incorporated herein by reference.

Circulatory support or bypass system 10 is contemplated to supplement or totally replace the pumping function of the heart during cardiac surgery and/or during temporary periods of heart failure. The system 10 can also be used during medical emergencies such as trauma, heart attack or heart failure. Circulatory support system 10 is particularly contemplated for patients in need of partial bypass of the left side of the heart while oxygenation of the blood may be maintained with the patient's own lungs. Support system 10 is advantageously arranged to be a portable unit which facilitates handling and reduces cost and incorporates a portable control unit discussed in greater detail below.

Figure 3:
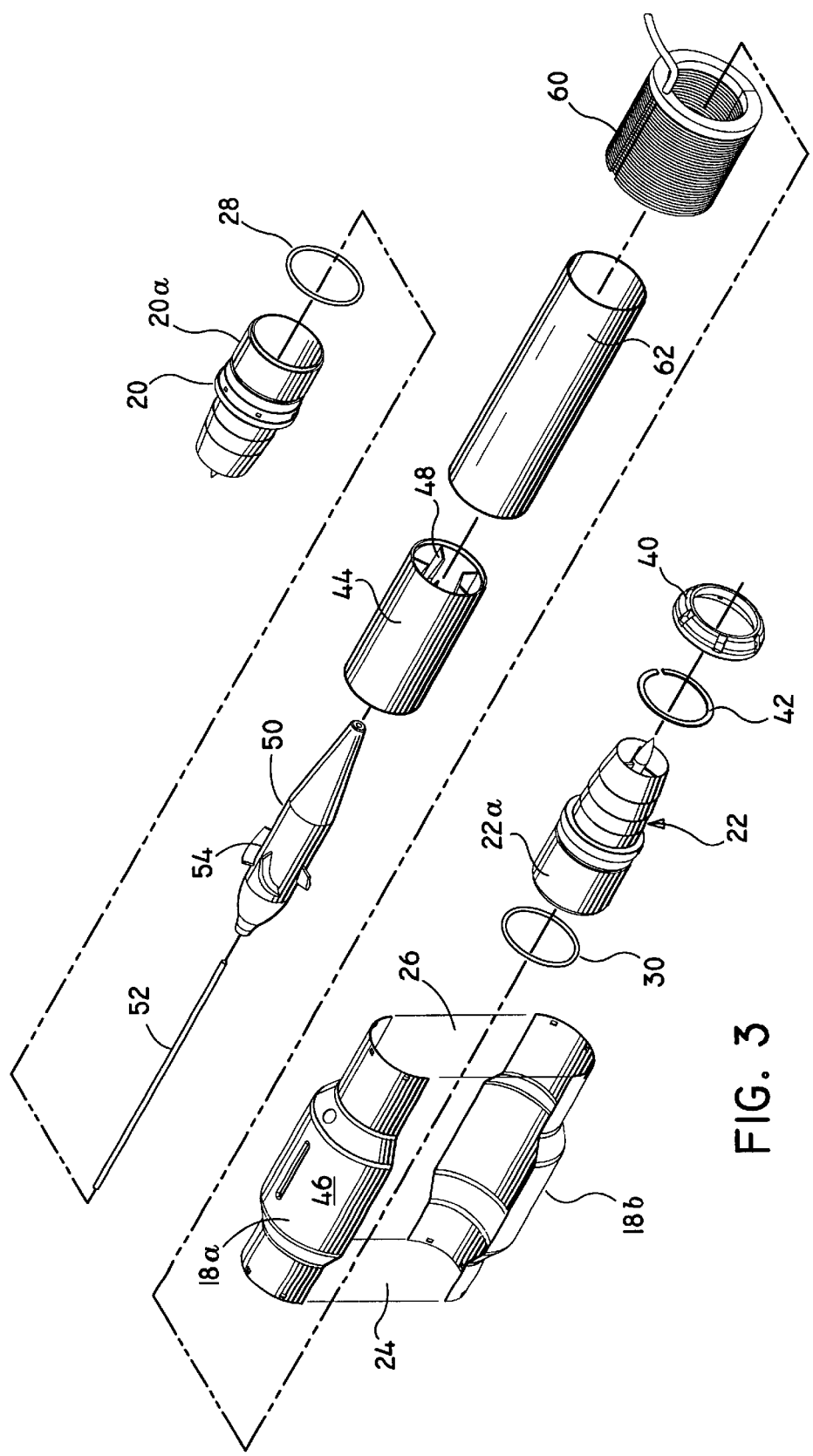
FIG. 3 is a perspective view with parts separated of the portable pump.
Figure 4:
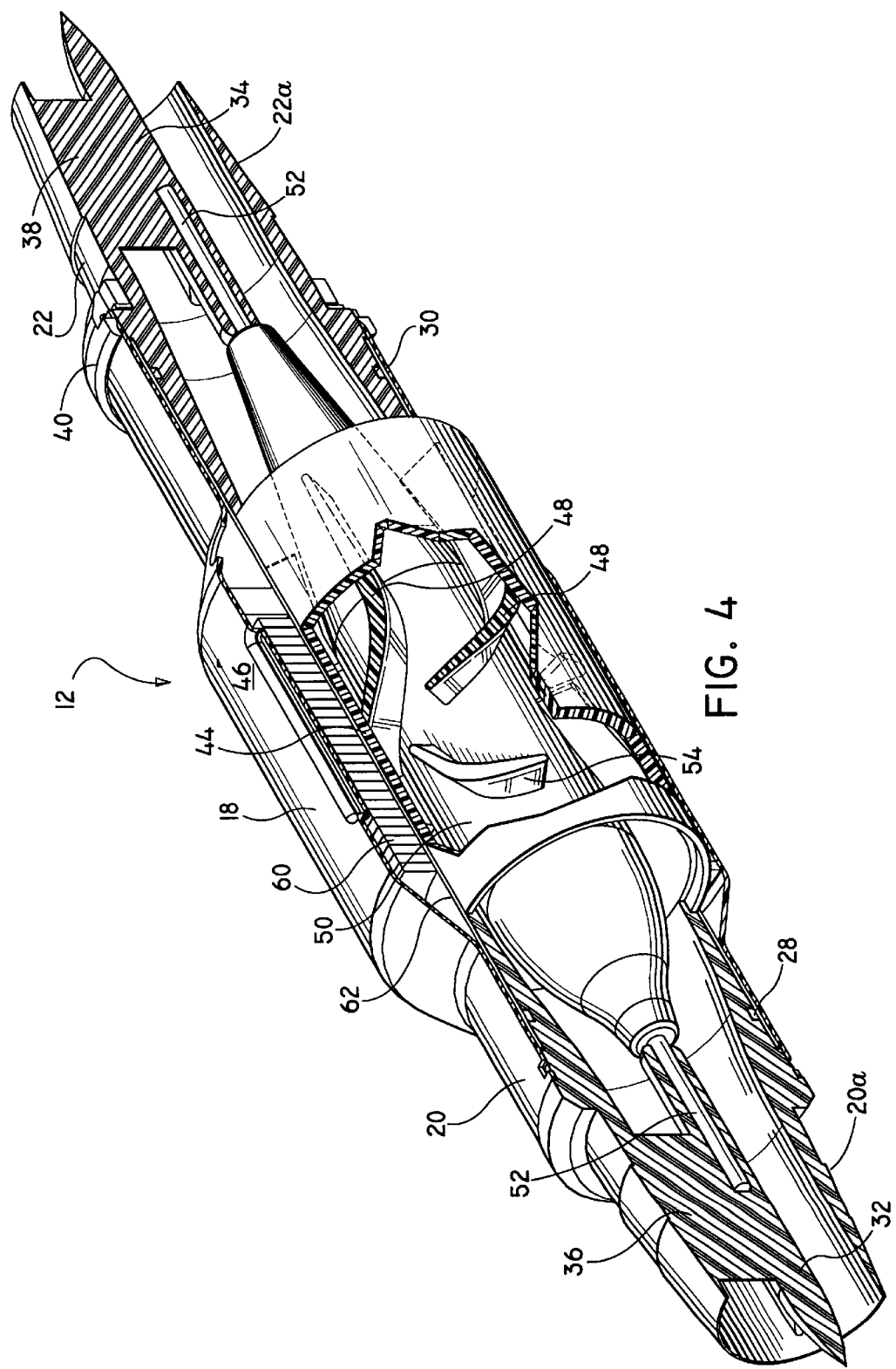
FIG. 4 is a perspective view of the portable pump with portions cut away and in cross-section.
Figure 7:
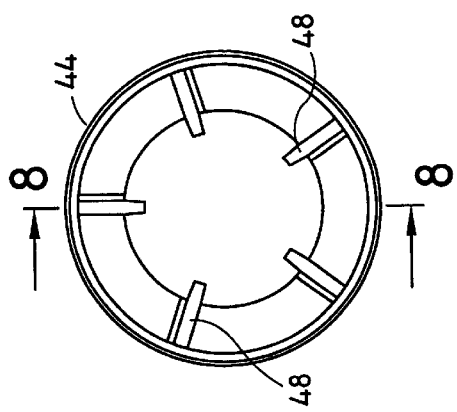
FIG. 7 is an axial view of the stator housing illustrating the arrangement of the stator blades.
Figure 8:
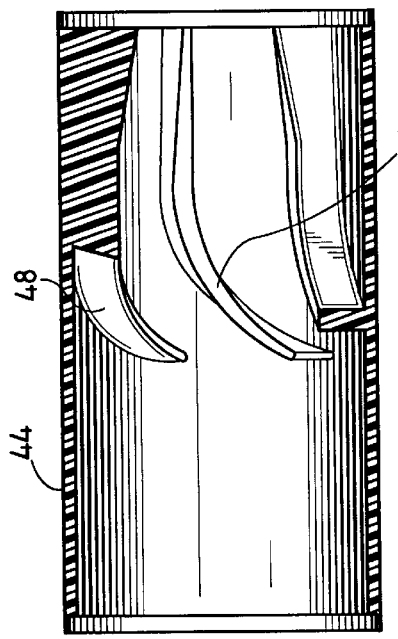
FIG. 8 is a cross-sectional view of the stator housing taken along the lines 8—8 of FIG. 7.

Referring now to FIGS. 1–4, support system 10 includes an axial flow pump 12 and inlet and outlet cannulated tubes 14, 16 associated with the axial flow pump 12. Inlet and outlet sections 14, 16 will be discussed in greater detail below. As best depicted in FIGS. 3–4, axial flow 12 pump includes pump housing 18 composed of housing half sections 18a, 18b secured to each other with the use of adhesives, screws or the like. Inlet and outlet connectors 20, 22 are respectively mounted within inlet and outlet openings 24, 26 of pump housing 18. As can be seen, the inlet and outlet openings 24, 26 are in axial alignment although offset arrangements are envisioned as well. In a preferred arrangement, cylindrical mounting portions 20a, 22a of the respective connectors 20, 22 are positioned within sleeve 62 within the inlet and outlet openings 24, 26 of pump housing 18 and retained therein in a manner discussed in detail below. O-ring seals 28, 30 may be utilized to provide fluid tight seals between connectors 20, 22 and pump housing 18. Connectors 20, 22 respectively connect inlet and outlet cannulated tubes 14,16 to flow pump 12.

In a preferred embodiment, the length of the pump 10 ranges from about 3.0 inches to about 4.5 inches, more preferably, about 3.76 inches, and the diameter ranges from about 0.7 inches to about 2.0 inches, more preferably, about 1.2 inches. Other dimensions are contemplated which maintain the functionality and portability of the pump.

Figure 5:
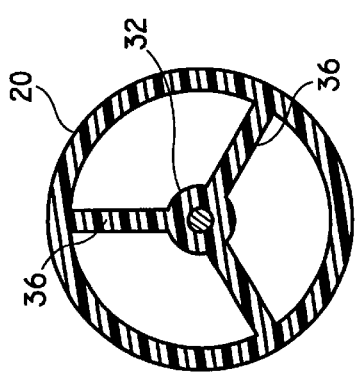
FIG. 5 is a cross-sectional view taken along the lines 5—5 of FIG. 2B illustrating the inlet straightener blades of the pump housing.
Figure 6:
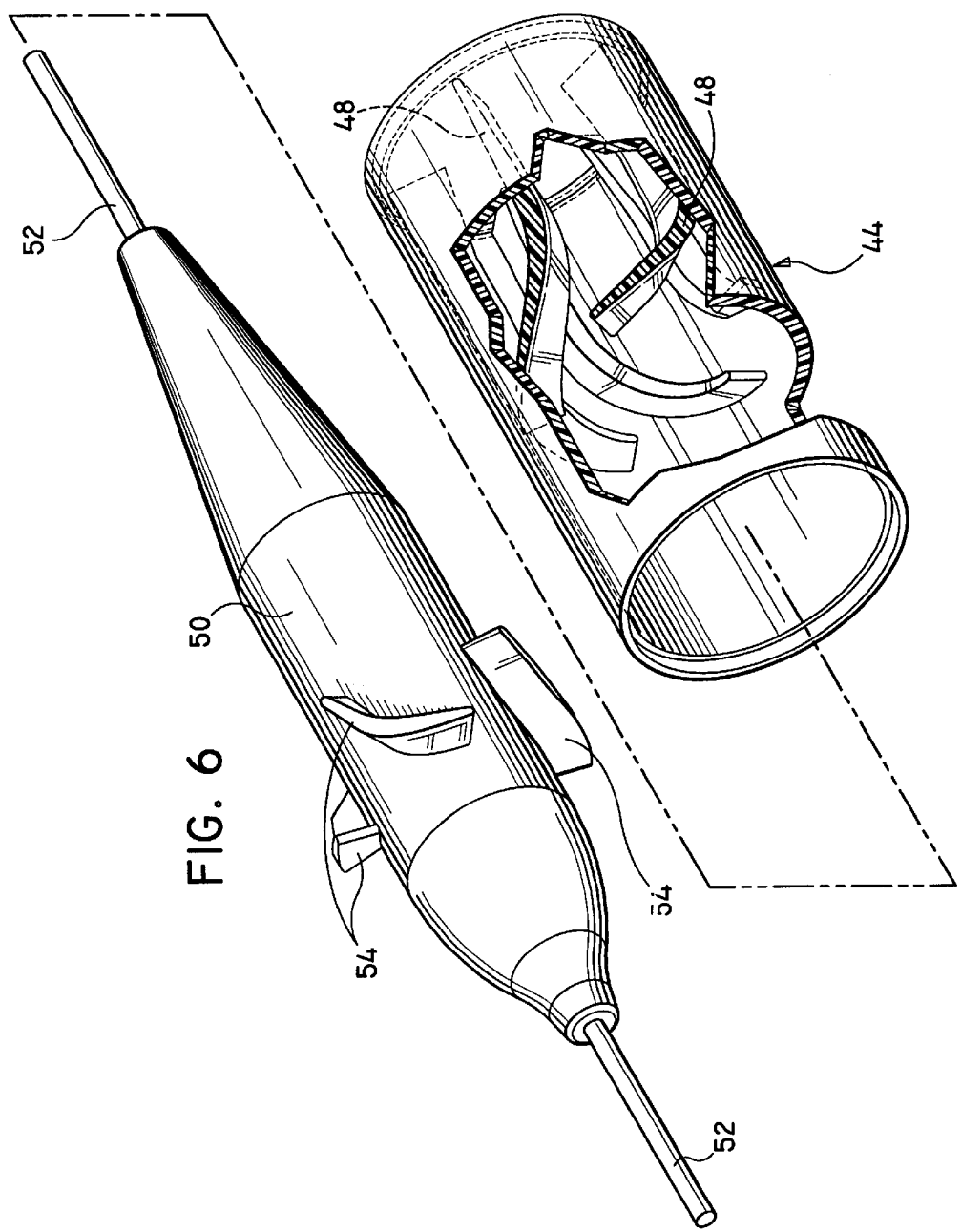
FIG. 6 is a perspective view of the impeller and the stator housing of the portable pump.

With particular reference to FIG. 4, inlet and outlet connectors 20, 22 include central interior hub portions 32, 34 respectively. Hub portion 32 of inlet connector 20 has inlet straightener blades 36 (e.g., 3) extending from the outer surface of the hub 32 to the inner surface of the connector 20 as also depicted in the cross-sectional view of FIG. 5. Similarly, hub portion 34 of outlet connector 22 has outlet straightener blades 38 extending from the outer surface of the hub 34 to the inner surface of the connector 22. Straightener blades 36 provide an axial flow effect on the blood entering flow pump to facilitate flow of the blood through the pump 12 to improve pump efficiency. Similarly, straightener blades 38 provide an axial flow effect on the blood exiting pump 12 to facilitate blood flow through outflow cannulated tube 16 and within the circulating system of the patient. However, blades 36, 38 are not required and may be substituted with one or more support struts which have little or no affect on the blood flow and may function to support bearings on which the impeller rotates.

As depicted in FIGS. 1–4, outlet connector 22 has snap ring 40 mounted about its periphery and retained thereon by spring clip 42. Snap ring 40 functions to snap onto housing 18 to retain outlet connector 22 onto the housing. Similarly, a snap ring (not shown) may be utilized to retain inlet connector 20 on housing 18, or, in the alternative, the connectors 20, 22 may be mounted to the housing 18 with the use of adhesives or the like.

Referring now to FIGS. 3, 4, and 6–9, pump housing 18 includes cylindrical stator housing 44 disposed in central portion 46 of the pump housing 18. Stator housing 44 may include four stator blades 48 attached to its interior wall. Stator blades 48 extend axially and also peripherally within the interior wall of stator housing 44 to define the generally serpentine configuration of the blades shown. Stator blades 48 provide a general axial flow type effect on the blood passing through pump housing 18.

Figure 9:
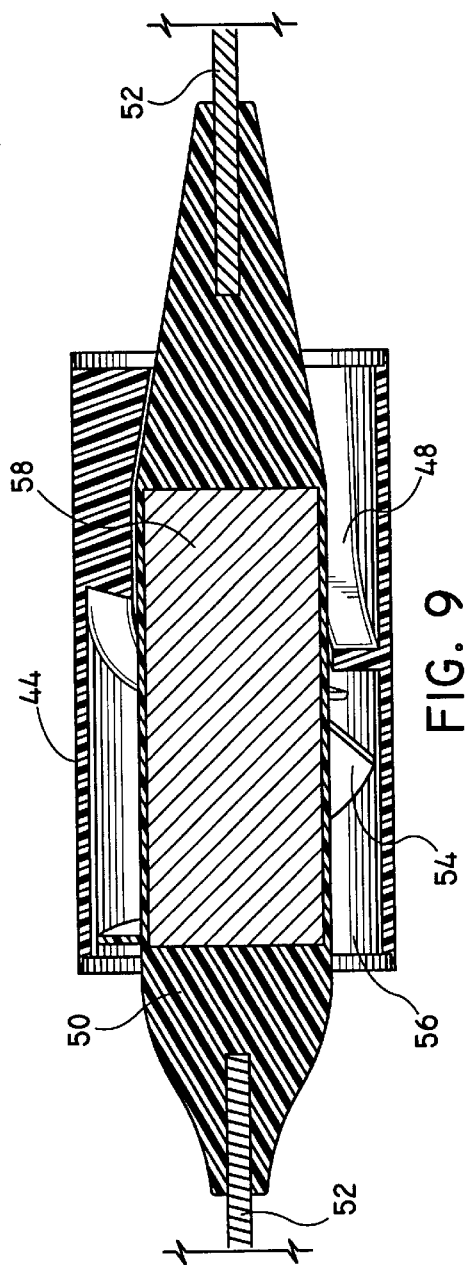
FIG. 9 is a cross-sectional view of the stator housing with mounted impeller.

An impeller 50 extends through stator housing 44 and is mounted via rotating shaft 52 to interior hubs 32, 34 of inlet and outlet connectors 20, 22, respectively. It is envisioned that bearings (e.g., sleeve) may be utilized to mount shaft 52. The bearings are preferably formed of polyethylene or the like. Impeller 50 has a plurality (e.g., 5) of impeller blades 54. Impeller blades 54 extend axially and circumferentially about the outer surface of the impeller 50 to provide an axial-flow pumping energy to blood entering pump housing. The outer surface of impeller 50 and the inner surface of stator housing 44 define an annular gap or blood path 56 through which blood passes through pump housing 18. Impeller 50 has a built-in 2-pole rotor magnet 58 as best depicted in FIG. 9. Blood flowing through this gap washes the bearings at the junction between the rotating and stationary components to cool the bearings and prevent thrombosis, thus avoiding having to provide a seal. In a preferred method of manufacture, impeller 50 is molded about shaft 52.

With reference again to FIGS. 3–4 and 9, the motor includes a motor stator 60 and rotor magnet 58. Motor stator 60 includes laminations and windings disposed between a sleeve 62 coaxially mounted about stator housing 44, and the interior wall of pump housing 18. Motor stator 60 is electrically connected to an external energy source. Stator 60 provides the appropriate electromagnetic forces to rotate the rotor magnet 58 and impeller 50. Thus, due to housing 44 and sleeve 62, the blood does not come into contact with motor stator 60. Motor stator 60 preferably has an outer diameter of about 0.70 inches to about 2.0 inches and preferably about 0.97 inches, thereby keeping the overall size of pump 10 relatively small.

Preferably, pump housing 18, stator housing 44 and impeller 50 are fabricated from a polymeric material and formed by conventional injection molding techniques. In a preferred arrangement all blood contacting surfaces are coated with an anti-thrombotic agent to prevent thrombosis development.

Figure 9B:
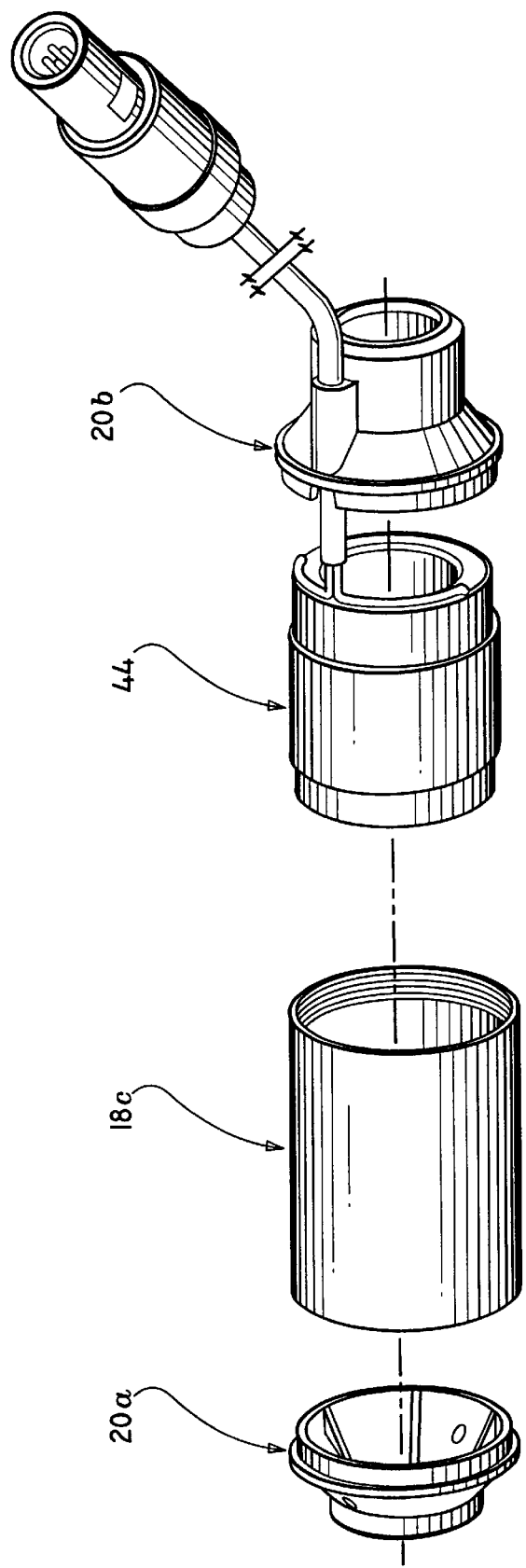
FIG. 9B is a perspective view of the outer housing components of the pump of FIG. 9A.

FIGS. 9A–9B illustrate an alternate embodiment of the axial flow pump of FIG. 1. In accordance with this embodiment, most of the components including the stator housing 44, impeller 50, etc. are substantially similar or identical to the prior embodiment. However, this pump includes an aluminum cylindrical housing 18C which replaces pump housing half sections 18a, 18b and inlet and outlet end bells 20a, 22a which are mounted to respective end portions of the pump housing. End bells 20a, 22a support inlet and outlet connectors 20, 22. This motor also includes sleeve bearings 55 mounted within hub portions 32, 34 of the connectors 20, 22 to mount shaft 52 for rotational movement. A thrust rod 57 is disposed at least partially within inlet bearing 55 to accommodate thrust loads experienced during operation of the pump. Shaft 59 extends the length of impeller 50 and defines an enlarged tapered section 59a adjacent the outlet end of the pump.

With reference again to FIG. 1, inlet and outlet sections 14, 16 will be discussed in detail. Each section 14, 16 includes respective flexible tubes 66, 68 connected to inlet and outlet connectors 20, 22 of axial flow pump 12 by a friction fit. In one illustrative embodiment, tubes 66, 68 preferably extend for a length of about 1–2 feet. Tubes 66, 68 may be spring reinforced to facilitate manipulation about the operative site. Preferably, at least a portion of outlet tube 68 is compressible for reasons to be appreciated hereinbelow.

Inlet and outlet cannulas 70, 72 are connected to the remote ends of flexible tubes 66, 68 through respective connectors 74, 76. Inlet cannula 70 has a blunt rounded end 78 for insertion into the patient's heart and a plurality of inflow ports 80 disposed in the side walls adjacent the blunt rounded end 78 to permit inflow of blood from the chamber of the heart. Outlet cannula 72 has an end 82 defining a bend therein which facilitates passage through a major vessel, e.g., aorta. End 82 may be straight as well. End 82 defines an outflow port 84 (shown in phantom) to permit blood to exit the outlet tube 68 under pressure. Inlet and outlet cannula tubes 70, 72 are also preferably made of a flexible material.

Connector 74 is a straight connector which retains inlet cannula 70 thereon by a friction fit. Connector 76 is a "T" connector having female threaded portion 89 to which is mounted stopcock valve 86. Stopcock valve 86 is a conventional valve having flow control handle 88 which rotates through manual manipulation to bleed or remove air from the system on the outlet side or section 16 of the system 10.

The system 10 further includes pressure sensor plug 90 associated with inlet section 14. Pressure sensor plug 90 is electrically connected to cable 92 which extends toward the remote end of inlet cannula 70 to pressure transducer 94 mounted to the outer surface of the inlet cannula 70. Pressure transducer 94 is utilized to detect pressure within the heart chamber.

The system 10 also includes pump control plug 96 which connects to the power source for energizing the pump 12.

Control Unit

Figure 10:
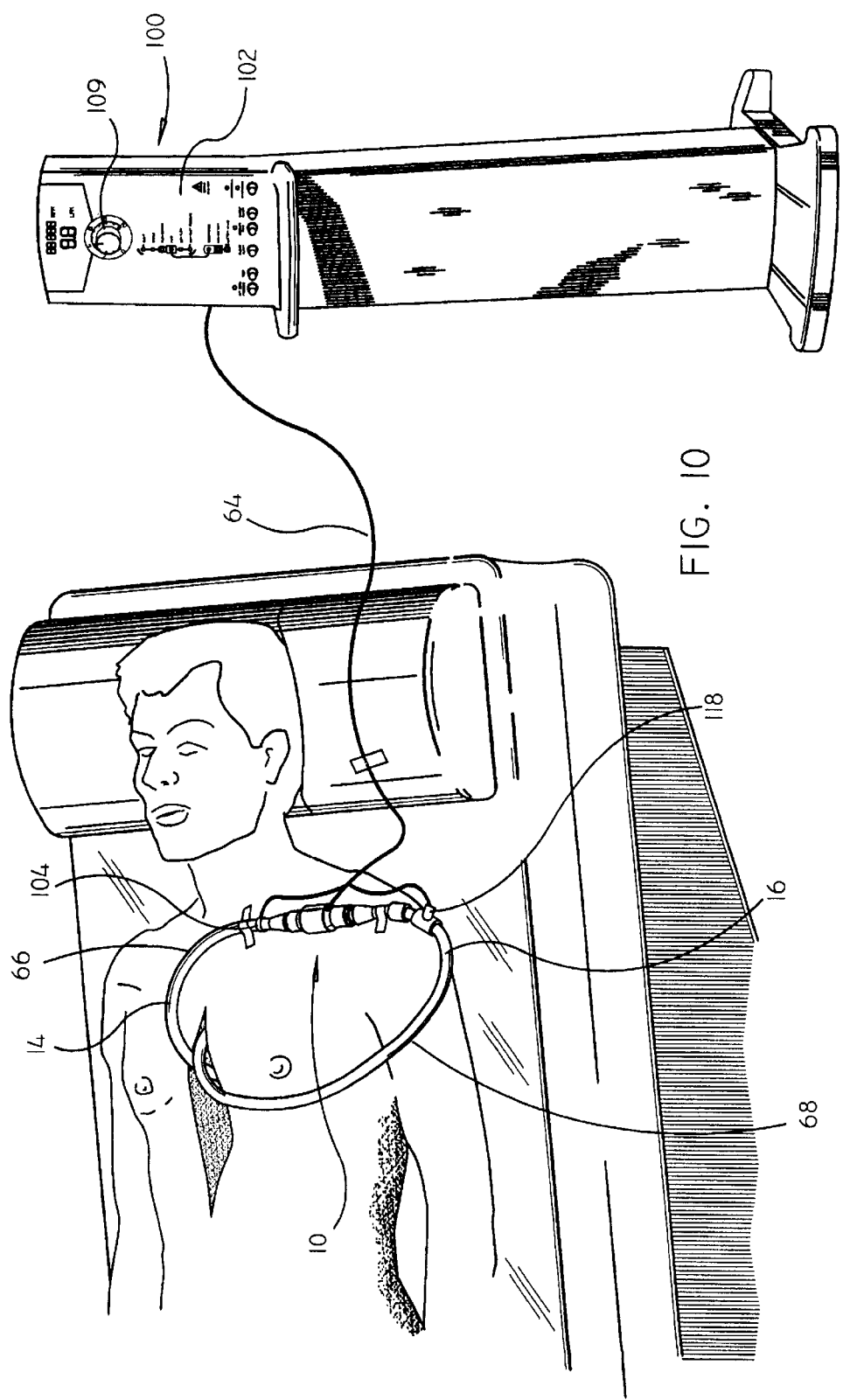
FIG. 10 is a view illustrating the system's control unit and use thereof in conjunction with supporting the pumping function of the heart of a patient.

Referring now to FIG. 10, a preferred control unit for use with the circulatory support system 10 will be discussed. Control unit 100 functions in controlling and monitoring the operation of the assist system and for sounding audible alarms for various conditions such as the presence of air bubbles in the bloodstream, low blood flow rate, and so forth. Control unit 100 is preferably mobile to facilitate hospital use. The control unit 100 includes a monitor/control panel 102 which provides readouts of blood flow rate and pump speed. Panel 102 includes a large knob 109 to allow an operator to control motor speed and hence, blood flow rate. Panel 102 also includes light emitting diodes, each of which is lit when an associated alarm condition exists. Control buttons on the front panel enable the operator to control various functions such as re-starting the motor. The control unit also preferably has a rear display panel identical to that of the front panel for displaying the same information, so that the system parameter and alarm information is visible from the rear as well as from the front of the control unit.

Blood flow rate is determined with a flowmeter/bubble detect sensor 104 clamped onto inflow tube 66. Sensor 104 shown schematically in FIG. 10 may be embodied as a conventional ultrasound flowmeter and bubble sensor packaged as a single unit. Preferably, the electronics are shared between the flow sensing and bubble detection functions to minimize the electronics and size. Generally, flow sensing is accomplished conventionally by transmitting and receiving ultrasound signals diagonally across the cannula in both the upstream and downstream directions, and comparing the phase of the upstream and downstream signals to ascertain the flow rate. The bubble detection is based on a measurement of the amplitude of the received ultrasound wave relative to the transmitted wave. If the amplitude of the received signal suddenly drops below a threshold, then the presence of an air bubble is indicated. Output signals generated by sensor 104 indicative of the flow rate and of the presence of air bubbles in the system are relayed back to controller 100 via dedicated wires within harness 64. Operating voltage to sensor 104 is also provided on the wire harness. A suitable flowmeter/bubble detect sensor 104 is available commercially from Transonic Systems Inc., located in Ithica, N.Y., Model No. H9X197. As an alternative, the flow sensor and air bubble detectors may be embodied as separate units.

Figure 10A:
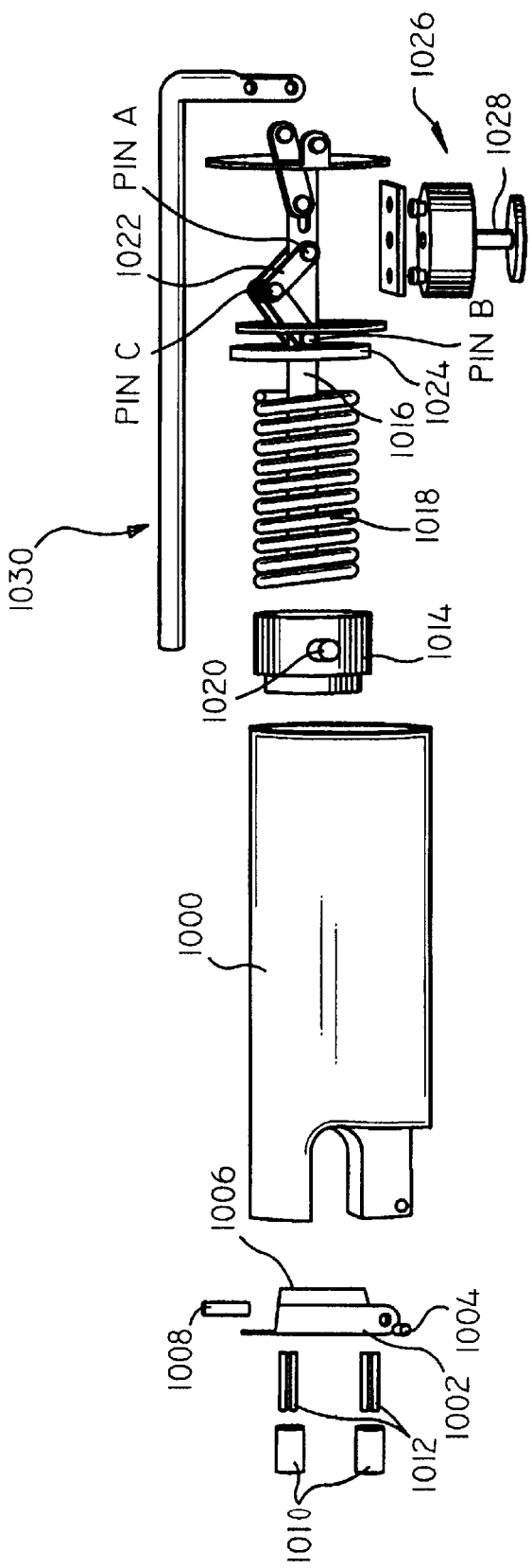
FIG. 10A is an exploded view of a clamp to be used with the control unit of FIG. 10.

A solenoid triggered cannula clamp 118 shown schematically in FIG. 10 is mounted on the output tube 68 of output section 68. When controller 100 determines that the blood stream contains air bubbles, based on the output signals provided by sensor 104, it sends an actuating voltage on harness 64 to the clamp 118 to cause it to clamp down on the output tube 68 to crimp the tube and prevent air from entering the bloodstream. One suitable clamp is shown in FIG. 10A. With reference to this Figure, the clamp (shown in exploded view) includes hollow cylinder 1000, left clamp 1002 pivotally mounted to the cylinder 1000 about pivot pin 1004 and defining clamping surface 1006, and latch pin 1008 which locks the left clamp 1002 in the open and closed position by reception within a corresponding opening (not shown) defined in the cylinder. A pair of finger grips 1010 and associated finger grip pins 1012 are mounted within respect to left clamp 1002. Finger grips 1010 and grip pins 1012 are depressed inwardly to release latch pin 1008 to permit opening of left clamp 1002 to position output tube 68 therein. The clamp further includes right clamp 1014 and retaining bar 1016 having distal bore 1018 to receive pin 1020 of right clamp 1014 to fixedly connect the two components. A link mechanism 1022 is mounted toward the proximal end of retaining bar 1016 and is fixed at its proximal end to retaining bar 1016 via pin A and at its distal end to stationary support plate 1024 via pin B.

Support plate 1024 is mounted to the proximal end of cylinder 1000 and defines an axial opening to permit reciprocal movement of retaining bar 1016. A solenoid 1026 is mounted adjacent link mechanism 1022 and includes solenoid plunger 1028 which moves upwardly upon actuation to engage link mechanism 1022, more particularly, pin C of the link mechanism 1022, to actuate the link mechanism to drive retaining bar 1016 distally. The clamp further includes a handle mechanism 1030 which resets the link mechanism 1022 to its rest position. In the drawing, link mechanism 1022 is shown in the actuated position. Prior to actuation, the link mechanism 1022 is in an overtoggled position (where the links of the linkage mechanism are in linear alignment) with the plunger 1028 resting on pin C. When a bubble is detected, the clamp is actuated which drives solenoid plunger 1028 of the solenoid 1026 upwardly, tripping the link mechanism 1022 to the position shown in FIG. 10A. During movement to this position, link pin A drives retaining bar 1016 and right clamp 1014 distally to thereby clamp tube 68 between left clamp 1002 and the right clamp 1014. To reset, the handle mechanism 1030 is pulled rearwardly. As the retaining bar 1016 is pulled to the right, the linkage mechanism 1022 will again over toggle ready to be tripped by the solenoid plunger. Another clamp suitable for this use is disclosed in U.S. Pat. No. 4,524,802 to Lawrence, the contents of which are incorporated herein by reference.

Referring again to FIG. 10, also included within wire harness 64 are wires that are routed to pressure sensor plug 90 (FIG. 1) which, in turn, is connected to wire 92 and pressure sensor 94 disposed at the distal end of inlet cannula 70, typically in proximity to the patient's heart. (The wires and sensor plug 90 are not shown in FIG. 10 for ease of illustration). These wires carry operating voltage to the pressure sensor 94 from control unit 100. The pressure sensor 94 provides an output signal representing the pressure sensed (also referred to herein interchangeably as "inlet pressure" of the pump 12). This output signal is routed to control unit 100 via wire harness "h". If inlet pressure is too low, motor speed is reduced to prevent suction occlusion.

Figure 11A:
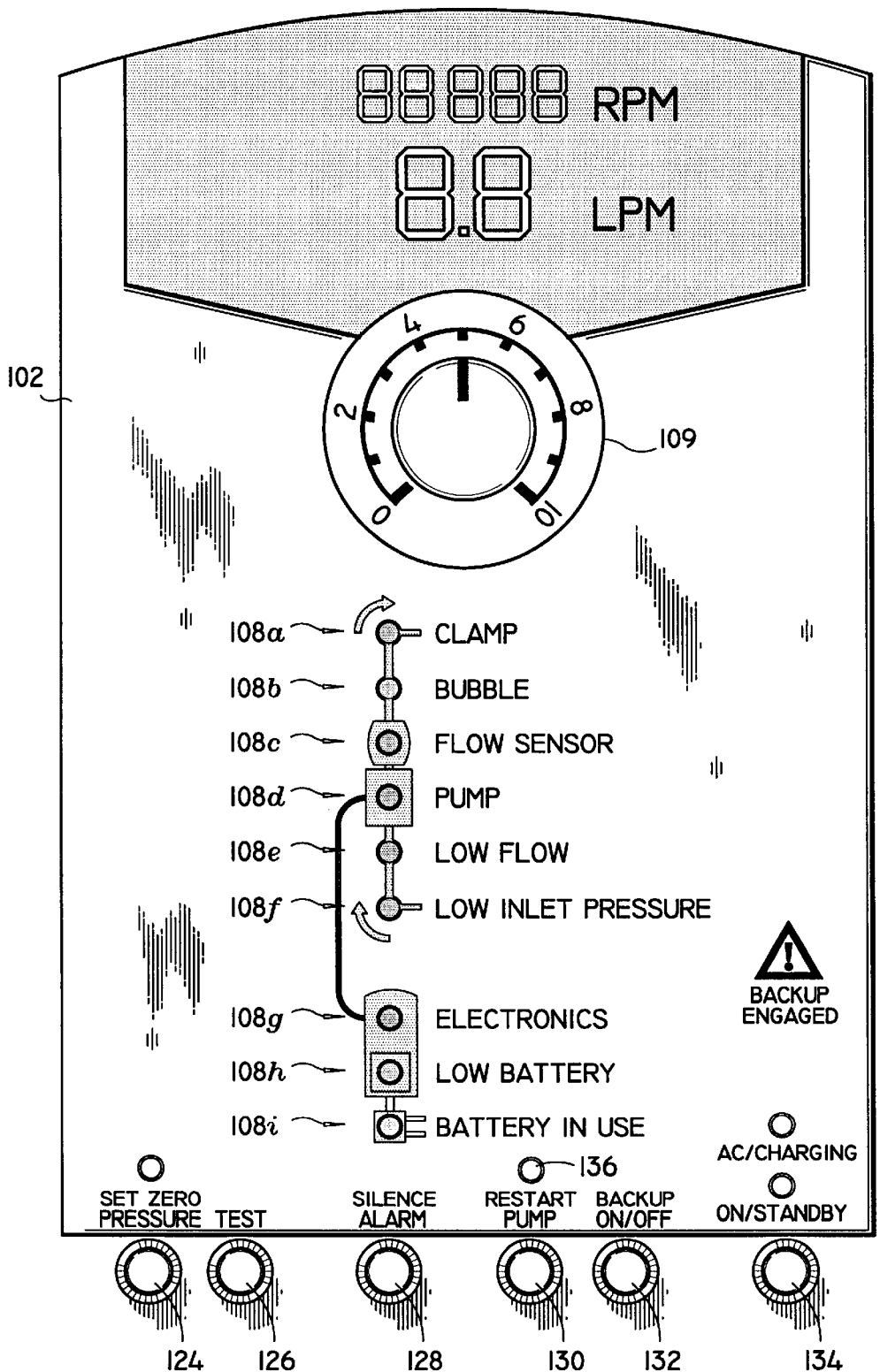
FIG. 11A is an illustration of an exemplary front panel for a control unit controlling operation of the pump.

With reference now to FIGS. 11(A–C) and 12, further details of the components of control unit 100 will be discussed. As shown in FIG. 11A, control panel 102 of the control unit includes LEDs 108a to 108i arranged in a "traffic status board" type layout. Push-button switches 124–134 are located at the bottom of the panel. A large dial 109 is manually rotatable to set motor speed. Readouts of measured motor speed in revolutions per minute (RPM) and measured blood flow rate in liters per minute (LPM) are digitally displayed directly above the dial.

Figures 11B, 11C:
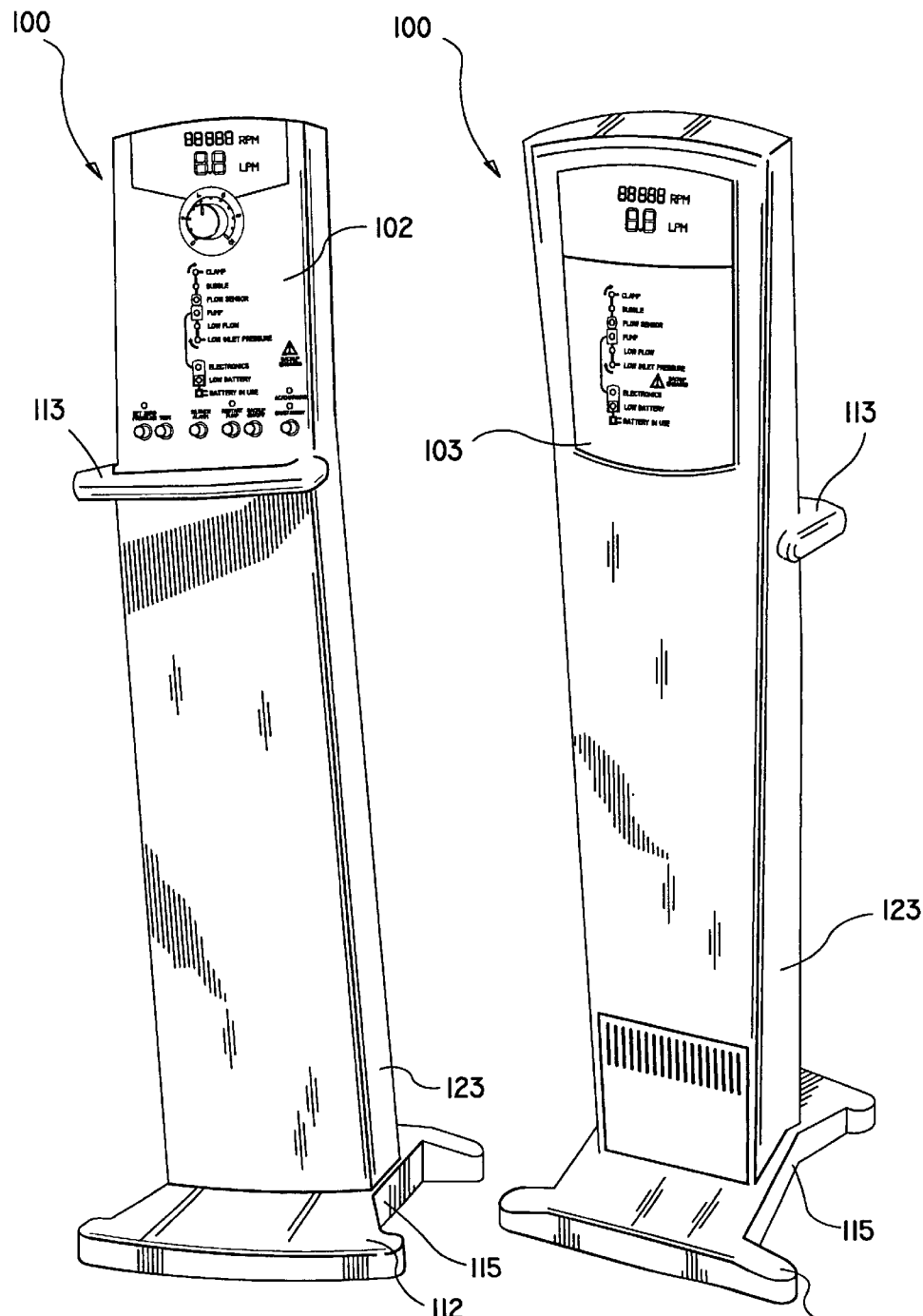
FIG 11B is a perspective view of an exemplary control unit showing the front portion thereof.
FIG. 11C is a perspective view of the exemplary control unit showing the rear portion thereof.
Figure 11D:
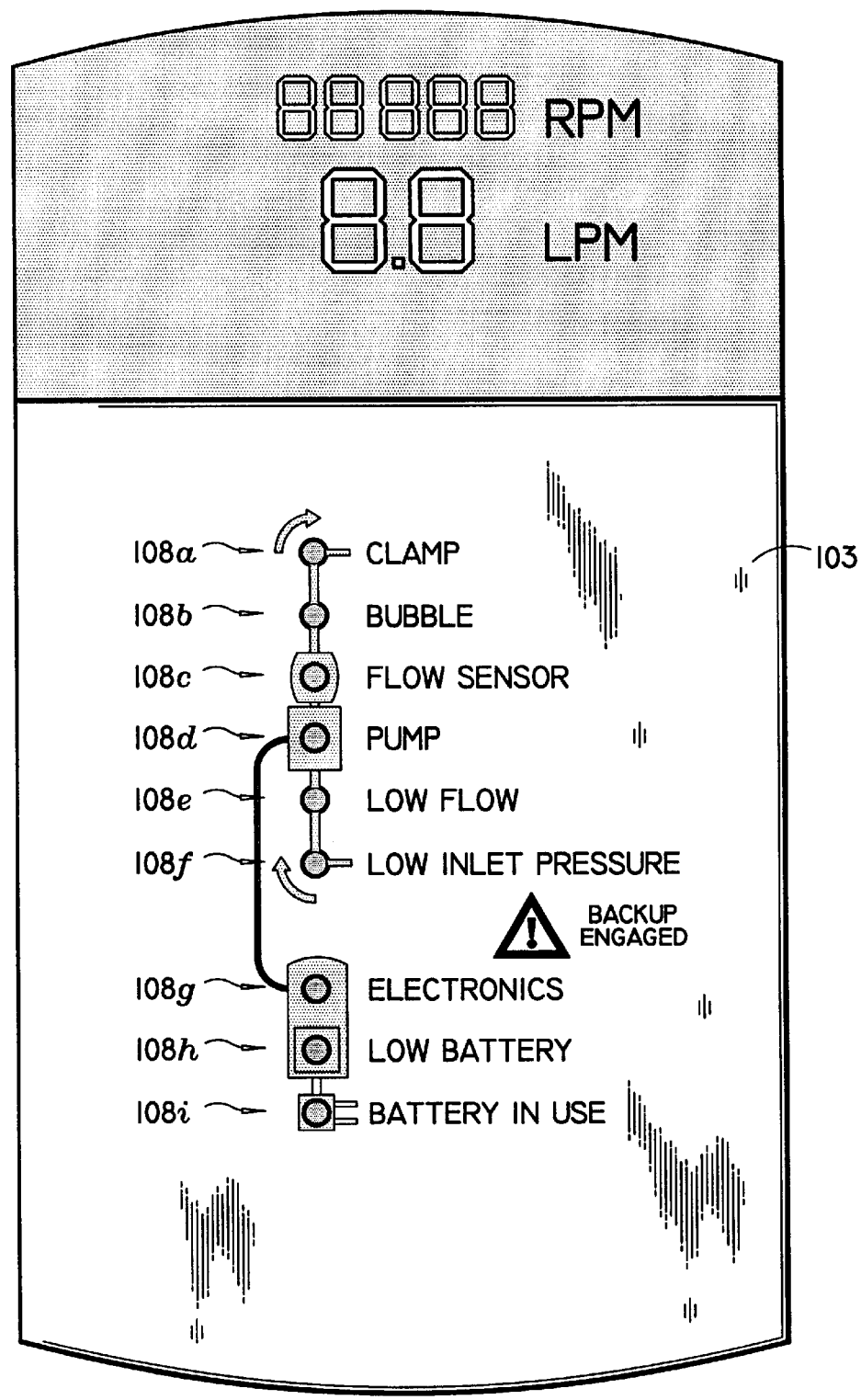
FIG. 11D is an enlarged illustration of the rear panel shown in FIG. 11C.

FIGS. 11B and 11C show respective front and rear perspective views of control unit 100. Unlike conventional hospital equipment, control unit 100 is embodied in the general shape of a long solid rectangle, with an exemplary height of about 48–50 inches, preferably, 54.5 inches, a width of about 7–12 inches, preferably, 9.7 inches, a thickness of only 3–7 inches, preferably, 5.5 inches, and with a suitable base support 112, preferably on wheels. Hence, control unit 100 is ergonomically designed to occupy a minimal amount of operating room space. Also, the height of the display panel 102 relative to the base support is high enough to prevent obstruction of the panel by the patient lying on the adjacent operating table. Base support 112 has side portions 115 that are approximately flush with the sides 123 of the main rectangular body of the control unit to conserve space. The front and rear portions of the base support each protrude about six inches from the main rectangular body. A handle 113 is provided on the front portion of the solid rectangular body.

A display panel 103 of preferably the same display format as the front panel 102 is provided on the rear of control unit 100, so that the alarm LEDs, motor speed and flow rate are visible from the rear as well as from the front of control unit 100. As such, visibility of the information by several personnel is facilitated. The motor speed control dial and push-button switches 124–134 are omitted from the rear display. Display panel 103 is shown in more detail in FIG. 11D.

Figure 12:
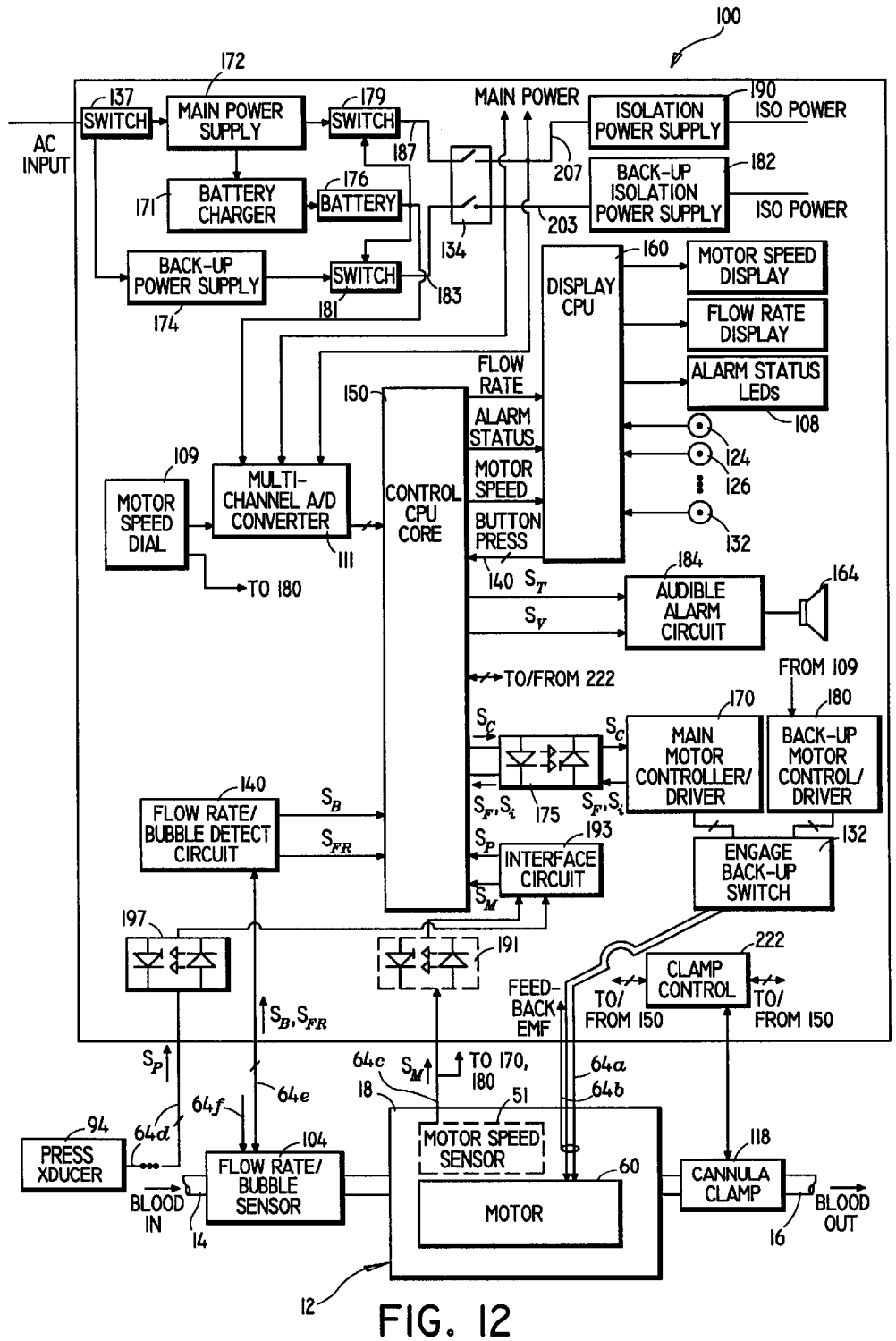
FIG. 12 is a block diagram illustrating the circuit components of the control unit and of the pump.

Referring to FIG. 12, control unit 100 includes a Control central processor unit (CPU) core 150 which receives input signals from various circuit components within the control unit and within pump 12, and, in response, provides appropriate output signals to implement a host of functions. A Display CPU 160 acts as an interface between Control CPU core 150 and each of the push-button switches 124–132, LEDs 108(a–i) and the motor speed and flow rate displays. A Main Motor Controller/Driver 170 provides the drive power to motor 60 responsive to a pulse width modulated (PWM) signal from Control CPU core 150. A back-up Motor Controller/Driver 180 is provided to control the motor in a manual mode during emergency situations, for example.

Figure 13:
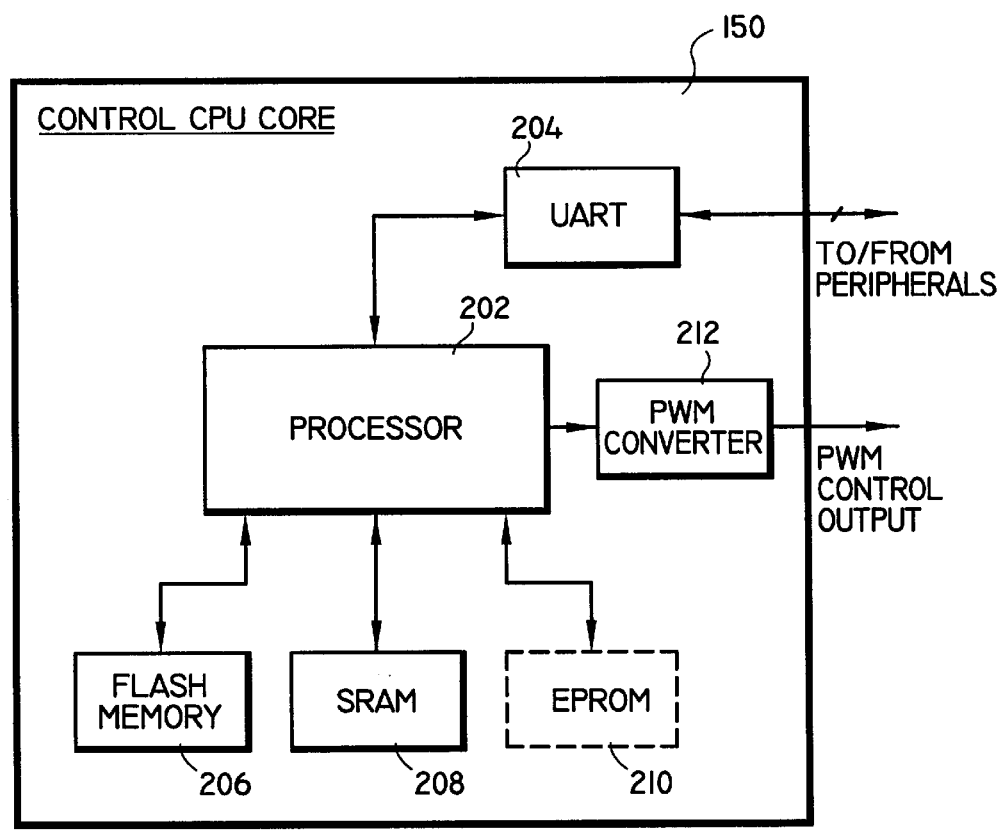
FIG. 13 is a block diagram of an exemplary Control CPU used within the control unit.

A simplified block diagram of Control CPU core 150 is presented in FIG. 13. A processor 202 such as Motorola MC 68332 communicates with the peripheral components such as Display CPU 160 by means of a Universal Asynchronous Receiver/Transmitter (UART) 204. Processor 202 contains a Time Processor Unit or PWM converter 212 which is used to generate a PWM signal for application to motor controller/driver 170 to control motor speed. Alternatively, a digital to analog (D/A) converter may be coupled to processor 202 and would provide an analog output voltage to control motor speed responsive to a digital word from processor 202. Control CPU core 150 and Driver CPU 160 are in constant communication via UART 204. (Display CPU 160 utilizes a similar UART therewithin). Each time Control CPU core 150 sends a "display" message, the Display CPU responds with a "key" message to indicate the status of the key presses. Typically this "key" message will indicate that no keys have been pressed and imply that the previous message was received. All messages may contain a checksum such that exclusive-OR of all the bytes results in 0x00. The Control CPU core and Display CPU may communicate using standard communications protocols, e.g., at 9600 baud, with even parity, seven data bits, one stop bit and without handshaking lines. Control CPU 150 also includes SRAM 208, e.g., 256 Kbit or higher, which may be used to store measured data as well as for storing parameters during computations performed by processor 202. Processor 202 also retrieves various parameter information such as threshold data stored in optional EPROM 210 (e.g. 64 Kbit×16) or within flash memory 206.

In operation, referring again to FIG. .12, depression of AC power switch 137 switches AC line voltage to main power supply 172 as well as to back-up power supply 174, each of which rectify the AC to provide DC output voltages (e.g. 8–15V DC) for powering the various circuit components of the system. Main power supply 172 also supplies voltage to a battery charger circuit 171 which charges battery 176. A switch 179 detects voltage output from main power supply 172 and, if it is within a predetermined voltage range, switches this voltage to output line 187. If switch 179 detects that the voltage output from power supply 172 is out of range, it switches voltage from battery 176 to output line 187. In either case, the voltage output on line 187 is provided to a push-button controlled relay 134. Likewise, switch 181 detects voltage from back-up power supply 174, and if this voltage is within the predetermined range, it switches the voltage to its output line 183. Otherwise, switch 181 switches the battery voltage from battery 176 to its output line 183. Switches 179 and 181 are preferably diode switches.

When relay 134 is activated, the DC voltages on lines 183 and 187 are switched to respective output lines 203 and 207. The voltage on these lines are provided as main power to CPU core 150 and CPU 160 and other circuit components of control unit 100. Each circuit component receiving main power will utilize the operating voltage from either line 207 or 203.

Isolation power supply 190 includes a DC to DC converter to convert the voltage on line 207 (if present) to a higher voltage (e.g., 24V DC) to provide isolated power. The purpose of the isolated power is to diminish the possibility of electric shock to the patient undergoing treatment. As such, the isolated power is supplied to the circuit components which are directly coupled to sensors which may contact the patient or the patient's blood. Hence, isolated power is supplied to Motor Controller/Driver 170, pressure transducer 94, flow rate/bubble sensor 104, cannula clamp 118, and optional motor speed sensor 61. The main power at the output of switch 134 is supplied to the remaining circuit components of the control unit.

When relay 134 is activated, output voltage on line 203 is also provided to back-up isolation power supply 182, which provides back-up isolation power to back-up Motor Controller/Driver 180 and to the engage back-up switch 132.

A multi-channel A/D converter 111 (e.g., eight channels) is coupled to the battery 176 and to output lines 203 and 207, and converts the respective voltages at those points to digital output signals which are supplied to CPU core 150. From the digital signal associated with the battery, CPU core 150 determines whether the battery voltage is below a predetermined threshold. If so, it commands Display CPU 160 to light the "Low Battery" LED on the display. CPU core 150 also determines from the digital outputs whether the battery is in use. If it is, CPU core 150 provides a corresponding alarm command to CPU 160, which then causes the "Battery in Use" LED 108i to light.

A/D Converter 111 is also coupled to motor speed dial 109 and provides CPU core 150 with a digital output indicative of the dial position. In response, CPU core 150 outputs a PWM signal $S_c$ (produced by the PWM converter therein) to Motor Controller/Driver 170 through opto-coupler array 175.

This opto-coupler array is used for isolation purposes to prevent voltages from within CPU core 150 from accidentally causing electric shock to the patient. Other isolation techniques such as transformer-coupled isolation may alternatively be used. Motor Controller/Driver 170 includes processing and drive circuitry to vary the drive voltage provided to motor 60 on leads 64a responsive to the PWM of signal $S_c$, in order to control motor speed and starting or stopping of the motor.

If the "engage back-up" switch 132 is depressed, then Back-up Motor Controller/Driver 180 is utilized to drive the motor 60. The Back-up Controller/Driver 180 does not receive motor control signals from CPU core 150, but rather, it is directly coupled to the motor speed dial 109 and controls motor speed in accordance with the dial position. Switch 132 switches the voltage output from the appropriate Controller/Driver 170 or 180 to motor 60 via lines 64a. Thus, the "engage back-up" switch 132 is utilized when the operator desires to override the automatic control by the CPU core such that the motor speed is controlled manually. This manual operating mode is useful in emergency situations when the control unit cannot properly control blood flow under CPU core control.

A feedback EMF signal from the motor coils is provided back to both Controller/Driver 170 on line 64b and to Controller/Driver 180. The processor within Controller/Driver 170 or 180 determines the actual motor speed based on the feedback EMF signal, compares the actual speed with the desired speed according to signal $S_c$ (or according to the dial 109 position directly when the back-up Controller/Driver 180 is in operation), and adjusts the drive voltage provided on lines 64a to obtain the desired speed within a predetermined tolerance. The actual measured motor speed is continually or periodically communicated by Controller/Driver 170 to the Control CPU core 150 as signal $S_F$. Control CPU core 150 in turn transmits the motor speed information to Display CPU 160 to display the same on control panel 102.

Both Controller/Drivers 170, 180 include a current limiting circuit which limits current drawn by motor 60 to a predetermined maximum. If the maximum current is reached, this is indicative of the motor 60 or pump 12 malfunctioning. When maximum current is reached, Motor Controller/Driver 170 forwards a signal $S_i$ back to the Control CPU core 150 indicative of this condition. CPU core 150 responds by sending a message to Display CPU 160 to light the "pump" LED 108d and sound an audible alarm. However, this condition does not stop the motor. (The Back-up Controller/Driver 180 may also be designed to communicate this information back to CPU core 150).

Suitable controller chips which may be utilized within Controller/Drivers 170 and 180 to perform many of the above-described functions are commercially available from several manufacturers. Examples include U.S. Philips Corporation, located in Sunnyvale, Calif. (part No. Philips TDA-5140) or from Micro Linear Corporation, San Jose, Calif. (part No. Micro Linear 4425). Both of these controller chips operate as sensorless controllers which monitor the feed-back EMF from the motor coils to determine and control the motor speed. As an alternative, a controller used in conjunction with a motor speed sensor 61, e.g. a Hall effect sensor, could be employed. In this embodiment, feed-back EMF would not be used. Sensor 61 is positioned adjacent motor 60 and provides a signal $S_M$ indicative of the sensed motor speed on line 64c. This signal is routed to Motor Controller/Drive 170 (or 180) which derives the measured motor speed from the signal and then adjusts the voltage drive or pulse width modulation (PWM) signal to the motor accordingly to adjust motor speed. Signal $S_M$ is also provided to Control CPU 150 through opto-coupler 191 to enable the instantaneous motor speed to be displayed on the display panel as in the case above.

Attention is now turned to flow rate/bubble sensor 104. As discussed above, this sensor provides measurement of blood flow rate and monitors for bubbles in the blood, preferably using ultrasound. The existence of any bubbles greater than a predetermined size can cause a serious medical condition since air is being pumped into the bloodstream. Hence it is desirable for the operator/surgeon to be immediately apprised of a bubble condition whereupon it can be effectively remedied as soon as possible. In accordance with the present disclosure, if a bubble condition is sensed, the pump is immediately caused to shut down to allow the surgeon to instantly remedy the bubble condition such as by sucking out the bubble with a syringe. Following motor shut-down due to a bubble condition, the motor does not start again automatically, but must be manually restarted by depressing the restart pump button 130. In addition, immediately upon the detection of a bubble condition, control unit 100 sends a command to a clamp control circuit 222, which responds by providing an actuation voltage to the cannula clamp 118. The actuation voltage causes clamp 118 to clamp down on the output tube 68, thereby crimping the cannula or tube and preventing air bubbles from entering the patient's bloodstream.

In operation, operating voltage is supplied to flow/bubble sensor 104 on line 64f. Sensor 104 outputs a flow rate signal $S_{FR}$ and a bubble sense signal $S_B$ on lines 64e corresponding to the associated conditions within inlet cannula 14. The sensor output signals are supplied to Flow Rate/Bubble Detect Circuit 140, e.g., a circuit board product available from Transonic Systems Inc., model T109 circuit board. Circuit 140 communicates the sensor output signals $S_B$ and $S_{FR}$ to Control CPU 150 in a suitable format, and also provides control signals to sensor 104 to control its operation. signal $S_B$ indicates the presence of a bubble condition, Control CPU 150 immediately changes the voltage level of motor control signal $S_c$ (or transmits another signal) to command a shut-down of motor 60, whereby Motor Controller/Driver 170 causes motor 60 to cease rotation. Contemporaneously, Control CPU 150 sends a command signal to clamp control circuit 222 to initiate clamping by clamp 118 by providing a momentary actuation voltage thereto. An alarm signal is sent to Display CPU 160 which causes the "Bubble" LED 108b and the "re-start pump" LED 136 to light or blink. In addition, CPU 150 activates audible alarm circuit 184 by outputting a tone signal ST and a volume signal SV. The tone signal enables circuit 184 to produce audible output through speaker 164. The volume signal causes the audible output to be ramped up to avoid startling the surgeons/nurses. (It is noted here that the audible alarm circuit 184 is automatically activated by CPU 150 whenever any of the other alarm LEDs 108a–108i are lit. The "silence alarm" button 128 enables an operator to silence the audible alarm each time it occurs for any of the alarm conditions).

When the motor is shut down in correspondence with the bubble alarm, the operator may attempt to remove the bubbles from the cannula such as by sucking them out with a syringe. Thereafter, to restart the pump, the operator manually resets the cannula clamp, and depresses the Restart pump button 130, which causes the bubble alarm to be extinguished and the motor to be re-started to a speed in accordance with the manual dial 109.

In an alternative embodiment, the cannula clamp 118 and the associated clamp control circuit 222 are eliminated. In this case, a bubble alarm condition will still stop the motor as described above to permit the bubble condition to be remedied such as with a syringe. The motor will then be re-started only after the Re-start pump button 130 is manually activated.

The flow rate signal $S_{FR}$ outputted by sensor 104 is routed to CPU 150 in suitable format by detect circuit 140. CPU 150 routes the flow rate information to Display CPU 160 which causes it to be displayed on the panel 102. Control CPU 150 performs a software routine wherein the flow rate is compared to a threshold value "L1" stored in memory within the CPU. If the flow rate drops below "L1" for a predefined time period, e.g., below 2 LPM for more than one second, CPU 150 communicates a message to CPU 160 to light the "Low Flow" alarm LED 108e and sound an audible alarm.

Optionally, control unit 100 also monitors for flow blockage and generates a flow blockage alarm via a dedicated LED (not shown) and audio alarm if blockage is detected. In this case, CPU 150 stores flow rate data continuously and evaluates whether the flow rate has dropped unexpectedly in the absence of the speed dial 109 being moved (after the flow rate having been above a predetermined threshold such as one LPM). If the flow rate drops by a predetermined amount or percent, e.g., by more than 30% in less than two seconds, then the flow blockage alarm is activated. The flow blockage alarm is extinguished when the flow rate rises above a threshold, e.g., above one LPM.

Control unit 100 also communicates with pressure transducer 94 to ascertain the measured pressure in the transducer's location, e.g., in proximity to or within the atrium, or alternatively, within the inlet cannula in a position closer to pump 12. Pressure transducer 94 may be a conventional miniaturized transducer available commercially, e.g., from Ohmida Medical Devices, located in Madison, Wis. Alternatively, transducer 94 is embodied within a housing clamped to the outer surface of the inlet cannula, e.g., in proximity to the pump. Pressure transducer 94 receives operating voltage via leads 64d (which run within the outer sheathing of inlet cannula 14) and outputs a signal SP indicative of the pressure back to the control unit on another one of leads 64d. This signal is digitized and received by opto-coupler 197 and routed through interface circuit 193 to CPU 150 in suitable format. CPU 150 includes a software routine that stores measured pressure data and determines whether the instantaneous pressure has dropped below a predetermined threshold "P1", e.g., to less than 2 mm of mercury. If so, a message is outputted to CPU 160 to light the Low Inlet Pressure LED 108f. Contemporaneously, CPU 150 sends a command to Motor Controller/Driver 170 to automatically reduce the motor speed at a predetermined rate of reduction, in an attempt to automatically bring the pressure back. Motor speed continues to drop until the pressure rises above P1 (or above a higher threshold) for more than a predetermined time period, e.g., for more than 1.2 seconds. When this condition is satisfied, motor speed is then ramped up to a speed in accordance with the speed dial 109. (As an alternative, the motor speed is reduced to a predetermined speed, or by a predetermined amount, and is maintained at that lower speed until the pressure rises above a threshold, which is followed by motor speed ramp-up).

It is noted that control unit 100 may include means to manually calibrate or "zero" the pressure measurement. That is, when CPU 150 detects that the "Set Zero Pressure" push-button 124 on the panel is depressed, it reads the instantaneous value of pressure as outputted by transducer 94 and stores that value as the offset to be used whenever the pressure transducer is read. The pressure transducer is preferably zeroed in this manner by the operator each time the control unit is turned on and prior to the cannulas 14, 16 being attached to the patient.

Control unit 100 preferably includes a test mode to verify proper operation of the motor. The test mode is activated by depression of "Test" push-button 126 on the panel, whereupon CPU 150 will send a command to Motor Controller/Driver 170 to force motor 60 to run for, e.g. 10–15 seconds at varying speeds. In the test mode, the motor will run regardless of any alarm conditions. The alarm LEDs will still light, but the alarms will not be audible or prevent the motor from running during the test mode.

In addition, a Power On Self-test feature is provided whereby the control unit undergoes a self-test under the control of CPU 150 whenever power is initially turned on. If the CPU detects any error within itself or any of its peripherals, CPU 150 will not allow the unit to run. The self test preferably includes a RAM test to determine if the RAM is accessible and a ROM test to ascertain that the check sum of the code has not changed. A test for invalid readings from any sensor is also included, as well as a connectivity/continuity test and a display test. If there are any errors, the LED on the front panel corresponding to the faulty circuit component will be lit and all dashes displayed on the flow rate and motor speed displays. If there are no errors, none of the LEDs will be lit and all zeroes are preferably displayed on the flow rate and motor speed displays.

During system operation, checks are continually performed on various components to verify proper continuity and operation, and an alarm is generated if a fault is detected. For instance, the "flow sensor" LED 108c on the front panel is lit and an audible alarm is sounded if the flow sensor 104 is determined to be electrically disconnected from control unit 100, or if the bubble amplitude readings are below a predetermined threshold, indicating improper mounting or contact between the flow sensor and the tubing. The clamp control circuit 222 continually samples the continuity of the cannula clamp 118, and reports faults to the CPU 150. The "clamp" LED 108a is lit and an alarm sounded if continuity is deemed inadequate. The "electronics" LED 108g is lit and a buzzer activated if the control CPU 150 is not receiving adequate messages from the display CPU 160, or if any power supply voltages are out of specification. The control unit 100 also includes a connector (not shown) within the unit housing to enable connection to a personal computer (PC) to aid in the testing of the control unit. Communication with the PC may be transferred at, e.g., 9600 baud with no parity, eight data bits, one stop bit and without handshaking lines.

Figure 14A:
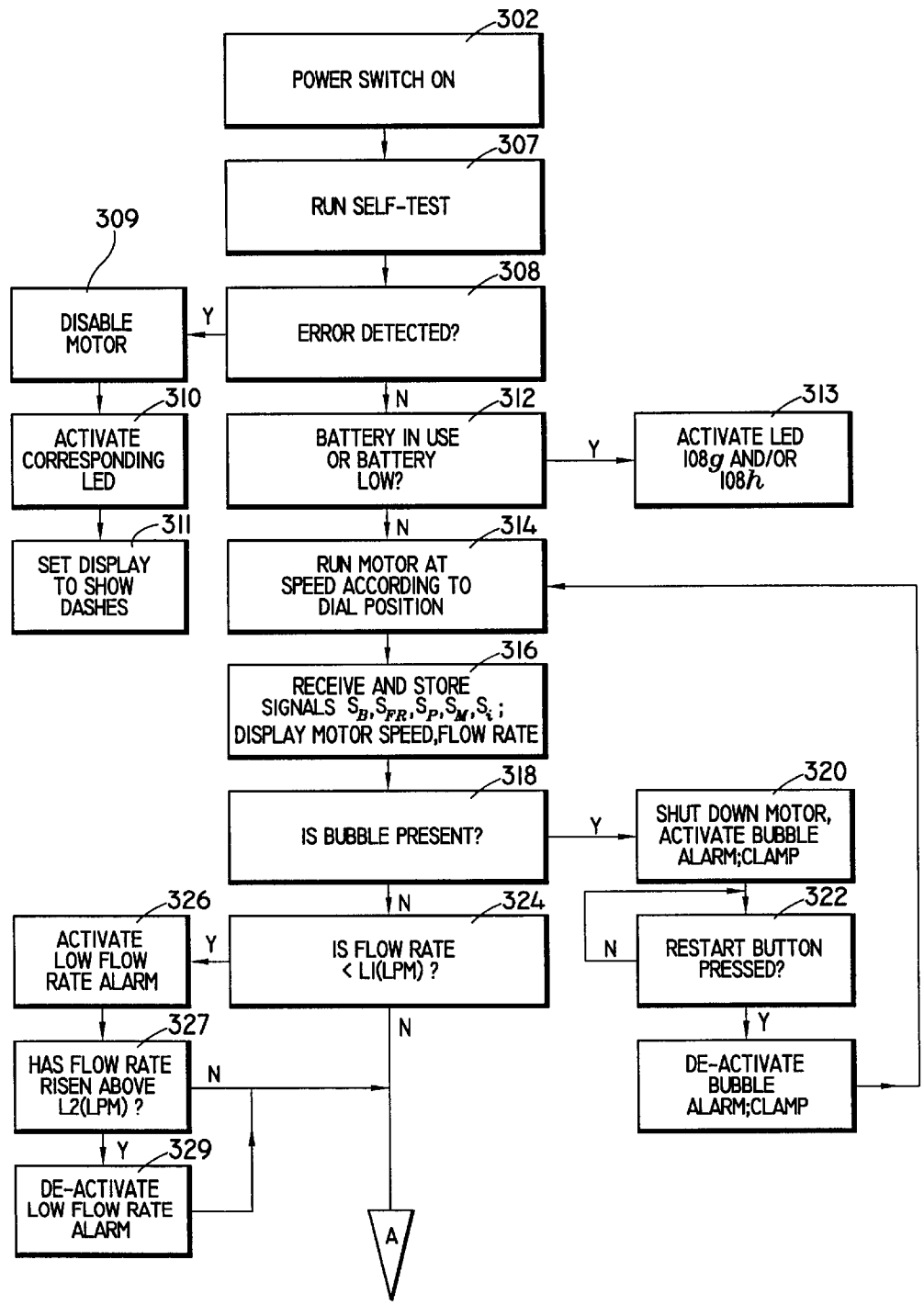
FIGS. 14A and 14B are flow diagrams illustrative of a software routine running within the Control CPU.
Figure 14B:
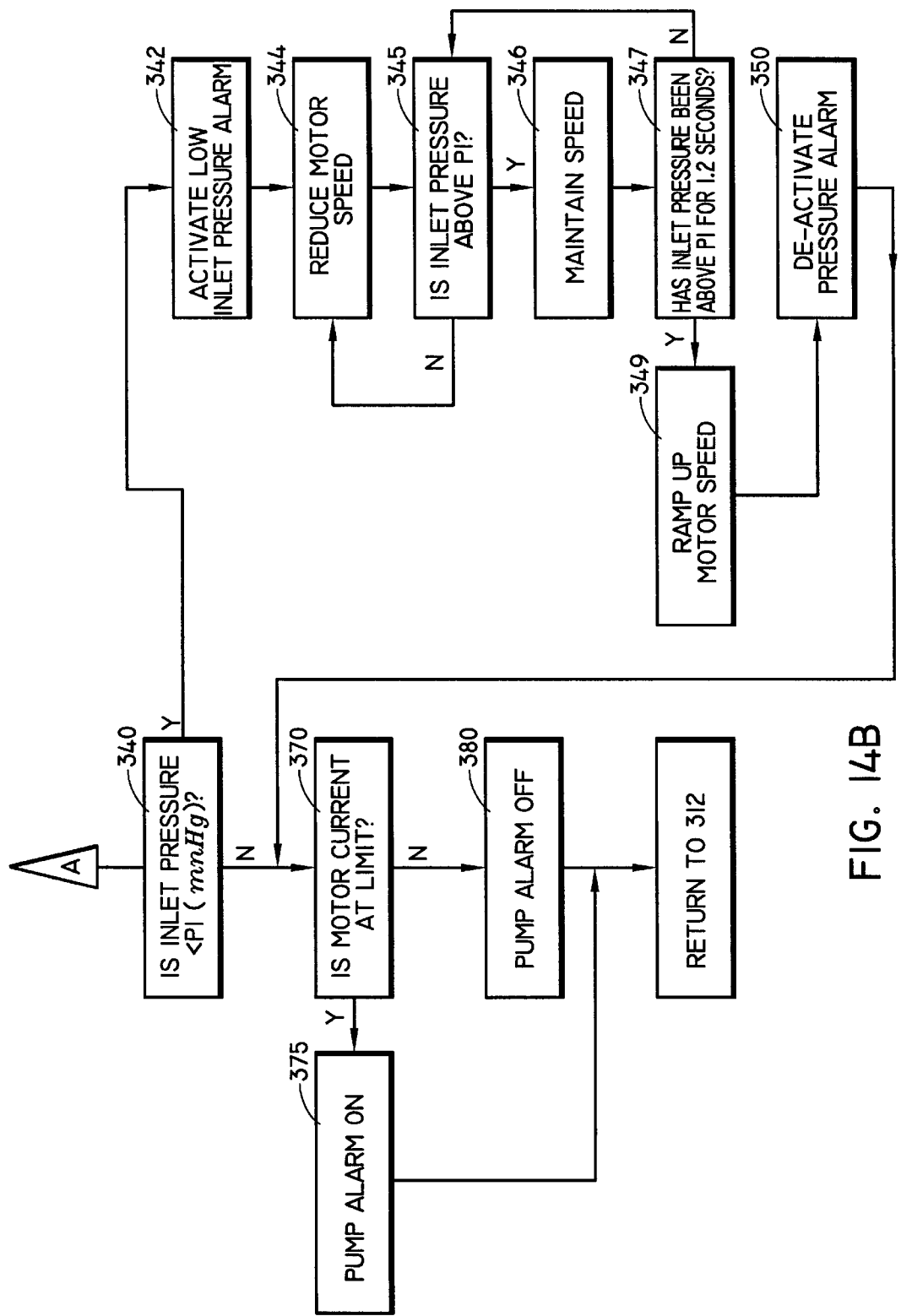

Referring now to FIGS. 14A and 14B, a simplified flow diagram illustrating operation of a software routine running on Control CPU core 150 is presented. Upon manual activation of the power switches (step 302) the Control CPU 150 performs the above-described self-test (step 307). If any errors are detected in step 308 the motor is disabled (step 309), the LED 108 on the panel associated with the faulty component will be lit (step 310) and the unit will be nonfunctional until the problem is corrected. Also, the motor speed and flow rate displays will show all dashes (step 311). If no errors are detected, the CPU core then determines in step 312 if the battery is in use or the battery is low, based on the digital outputs from A/D converter 111. If either condition is present, the corresponding LED is activated in step 313 by means of a command sent to Display CPU 160.

Next, CPU 150 determines the speed dial position in step 314 based on the output of converter 111, and forwards control signal $S_c$ to Motor Controller/Driver 170 to run the motor at the desired speed. With the motor running, bubble sense signal $S_B$, flow rate signal $S_{FR}$, pressure sense signal $S_P$, motor speed sense signal $S_M$ (or $S_F$) and current limit signal Si are transmitted to CPU 150 by the respective circuit components as discussed above (step 316). These signals may be received by the UART within CPU 150 and stored in the SRAM and/or flash memory. The motor speed and flow rate are determined based (on $S_M$ (or $S_F$) and $S_{FR}$, respectively, and commands are sent to the Display CPU to display the same on the display panel. The Control CPU then evaluates the bubble signal $S_B$ (step 318). If a bubble is determined to be present, the motor is shut down and the bubble alarm activated (step 320). At this point the CPU core detects whether or not the Re-start button has been pressed in step 322. When it is depressed, the bubble alarm is de-activated (step 323) and the software flow returns to step 314 where the motor is started again.

If in step 318 there is no bubble detected greater than a predetermined size, the next step is to ascertain whether the blood flow rate is less than the threshold level L1 (step 324). If so, the low flow rate alarm is activated in step 326. The alarm remains activated unless the flow rate rises above a threshold L2, e.g., 10% higher than L1 (steps 327, 329). The low flow rate condition does not stop the motor.

Next, in step 340 (FIG. 14B) the CPU core evaluates whether the inlet pressure has dropped below the threshold P1 (in mm Hg). If it has, the low inlet pressure alarm is activated (step 342) and the motor speed is automatically reduced in step 344. The motor speed reduction is carried out at a predetermined rate of reduction. If the inlet pressure is still below P1 in step 345, then the flow returns to step 344 where the motor speed is reduced further. The motor speed is incrementally ramped down in this manner until the inlet pressure rises above P1. When it does rise above P1, the motor speed is maintained at the latest reduced speed in step 346. Then, in step 347, if the inlet pressure is above P1 for a specified time interval, e.g. for 1.2 seconds, the motor speed is ramped up in step 349. Otherwise, the flow returns to step 345. Once the motor speed is ramped up in step 349 to a speed in accordance with the motor speed dial 109, the pressure alarm is de-activated in step 350 and the flow returns to step 370.

The next step (step 370) is to determine if the motor current is at the limit, based on the signal Si provided by the Motor Controller/Driver 170 or 180. If the limit is reached, the Pump alarm is turned on in step 375, otherwise, it is commanded off in step 380. The software flow then returns to step 312 where the diagnostic routine is repeated.

Preferred Arrangements for Connecting the Support System

Figure 15:
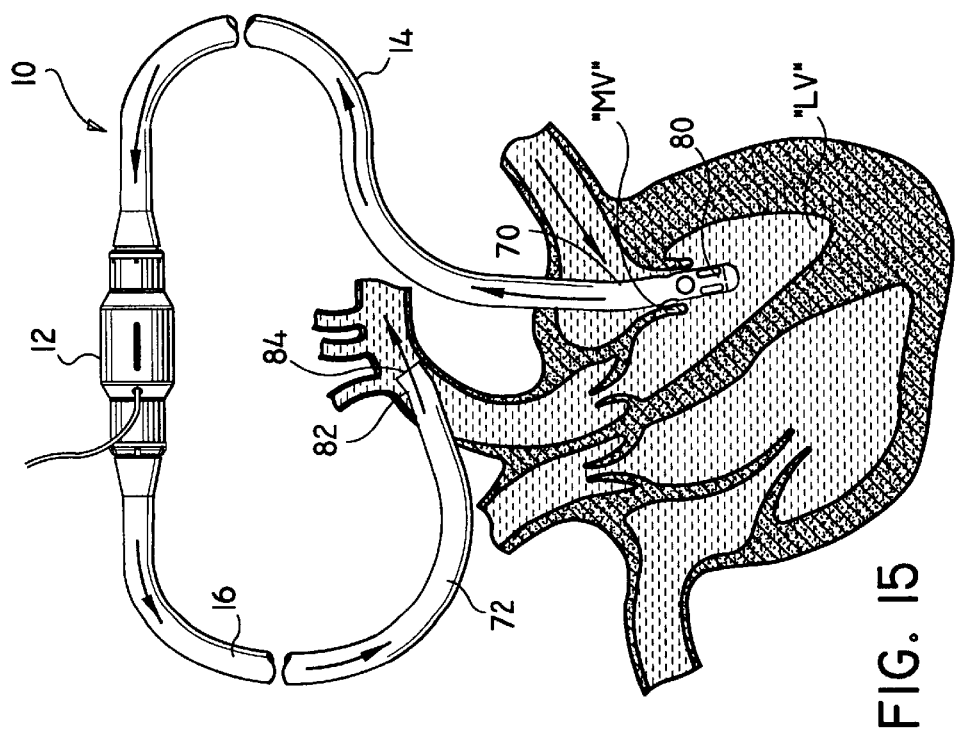
FIG. 15 is a view illustrating one method of application of the circulatory support system where the inlet cannula accesses the left ventricle of the heart through the mitral valve and the outlet cannula is disposed in the aorta.

Preferred arrangements for connecting the support system 10 will now be discussed. With reference again to FIG. 10, support system 10 is illustrated for use with an open (full medial) sternotomy which involves the splitting of the sternum bone to gain access to the heart. As discussed above, support system 10 is contemplated for use in assisting the left side of the heart while the blood flows through the right side to deliver blood to the lungs for oxygenation. As depicted, flow pump 12 of support system 10 is sufficiently small to be placed directly on the upper chest of the patient away from the sternal area and may be secured to the chest with conventional medical tape or secured to the drape with conventional surgical clips. Inflow and outflow sections 14, 16 are then appropriately positioned adjacent the chest cavity to access the heart and/or major blood vessels. With reference now to FIG. 15, one arrangement for connecting the system is described. Inlet cannula 70 of inlet section 14 is introduced through the heart wall and passed through the mitral valve "MV" with the inflow ports 80 positioned in the left ventricle "LV" as shown. Outlet cannula 72 is inserted through the aorta wall with the use of end portion 82 with the outflow port 84 positioned in a downstream position within the aorta "A". Upon operation of the system 10, blood is withdrawn from the left ventricle "LV" through inflow ports 80 of inflow cannula 70 and directed to the pump 12. Pump 12 imparts mechanical pumping energy to the blood and directs the blood under pressure through outflow cannula 72 and into the aorta "A", thus assisting the functioning of the left side of the heart. The blood is circulated throughout the body via the body's circulatory system and through the right side of the heart to the patient's lungs for oxygenation. During operation, monitoring, checking and controlling the system 10 is performed with control unit 100 to calculate flow rate, pressure within the heart, air bubble detection, etc . . . as discussed hereinabove.

Figure 16:
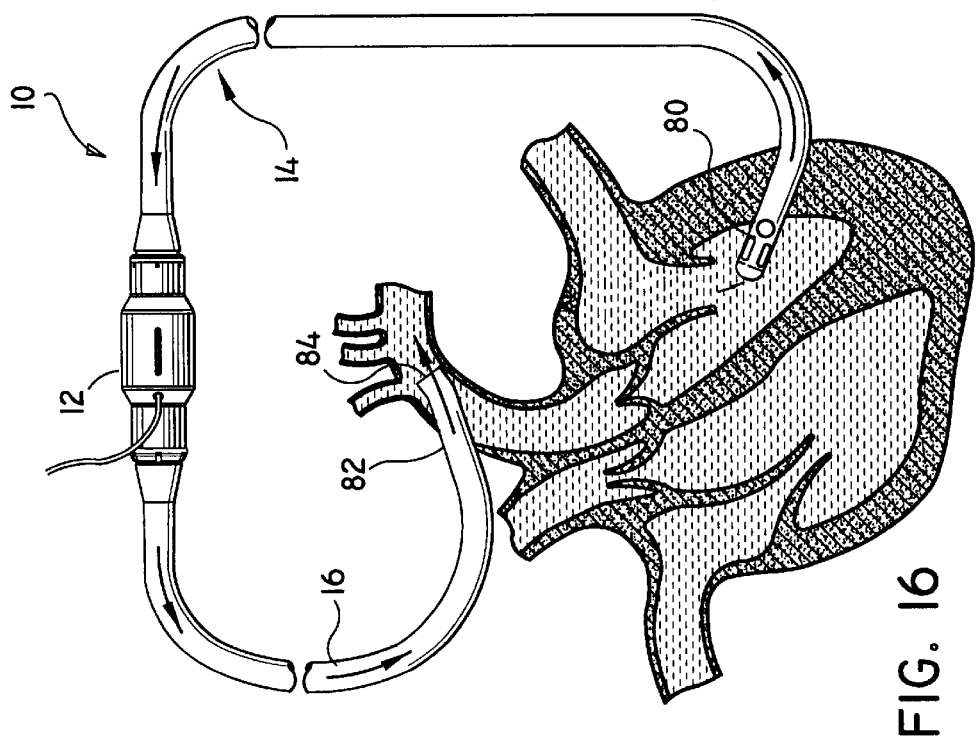
FIG. 16 is a view illustrating an alternate method of application of the circulatory support system where the inlet cannula accesses the left ventricle of the heart through the wall of the heart.

FIG. 16 illustrates an alternate method whereby the inflow cannula 70 accesses the "LV" through an incision formed in the wall of the heart.

Figure 17:
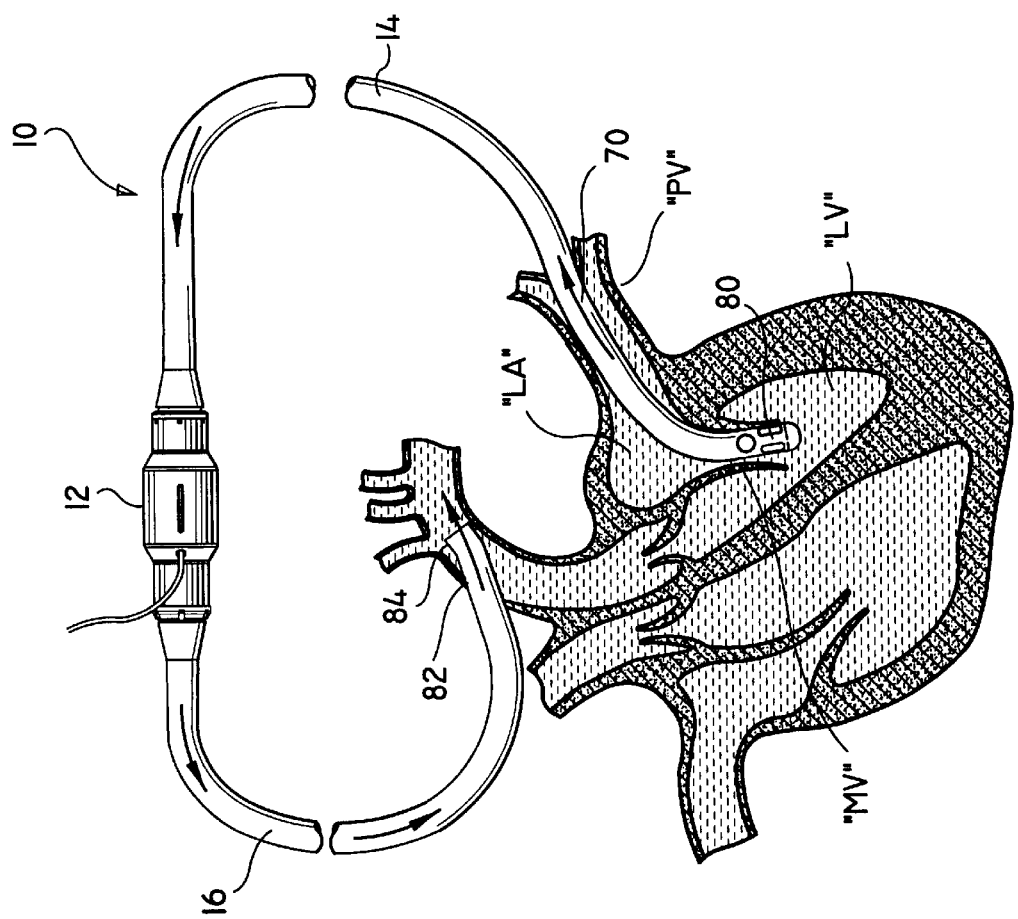
FIG. 17 is a view illustrating another method of application of the circulatory support system where the inlet cannula accesses the left ventricle through the juncture of the pulmonary veins and through the mitral valve.

FIG. 17 illustrates another alternate method of application of circulatory support system 10. In accordance with this method of application, inflow cannula 70 is introduced into the left ventricle "LV" through the region adjacent the juncture of the pulmonary veins "PV" (left or right) and passed through the mitral valve "MV" with the inflow ports 80 of the tube 70 located within the left ventricle "LV".

Figure 18:
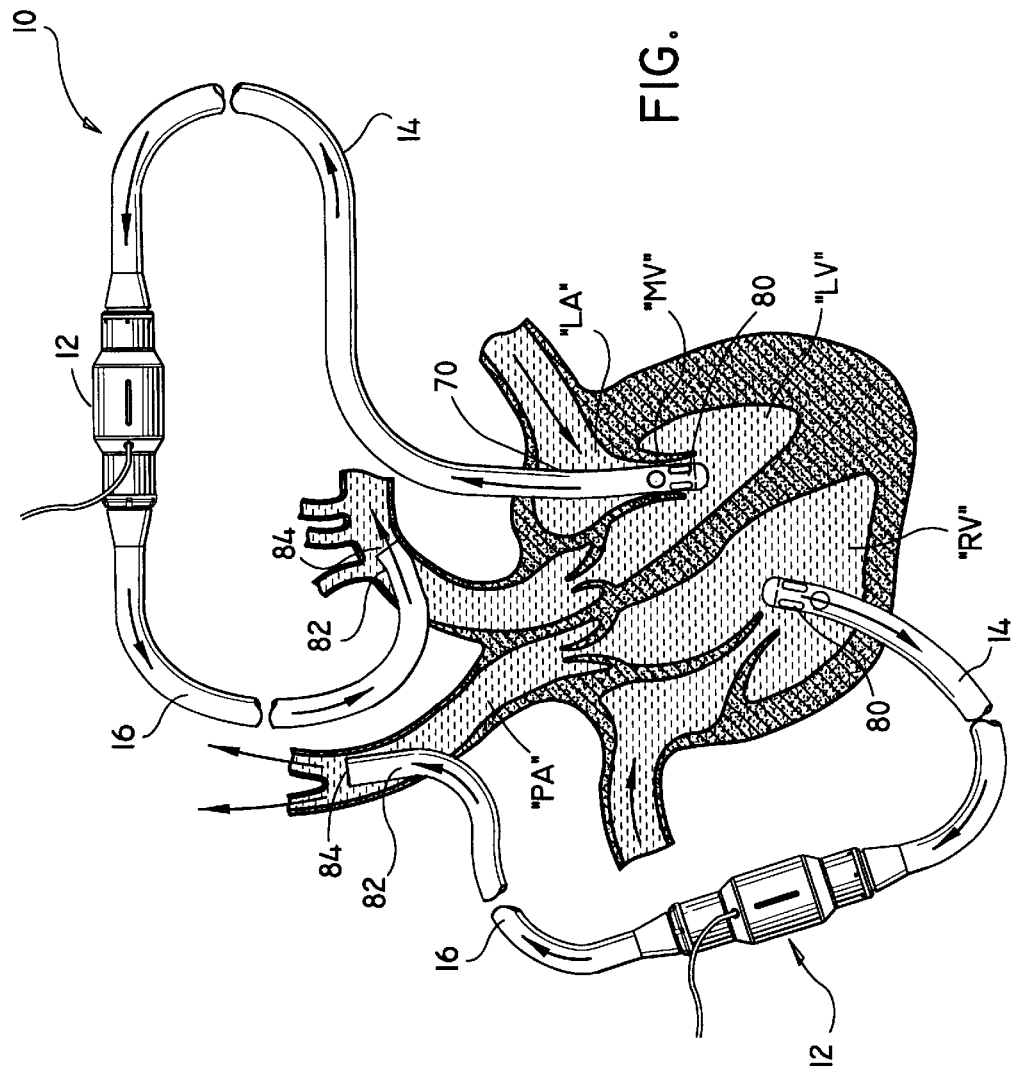
FIG. 18 is a view illustrating the use of a second circulatory support system for assisting the right side of the heart.

FIG. 18 illustrates an alternate method of application where two support systems are used for total heart bypass. The support system utilized for bypass of the left side of the heart is identical to that described in connection with FIG. 15. The support system utilized for right heart bypass has its inflow cannula 70 inserted through the heart wall with the inflow ports 80 positioned in the right ventricle "RV". The outflow cannula 72 is positioned in the pulmonary aorta "PA" in downstream orientation as shown. In this application, the lungs are still utilized to oxygenate the blood.

Figure 19:
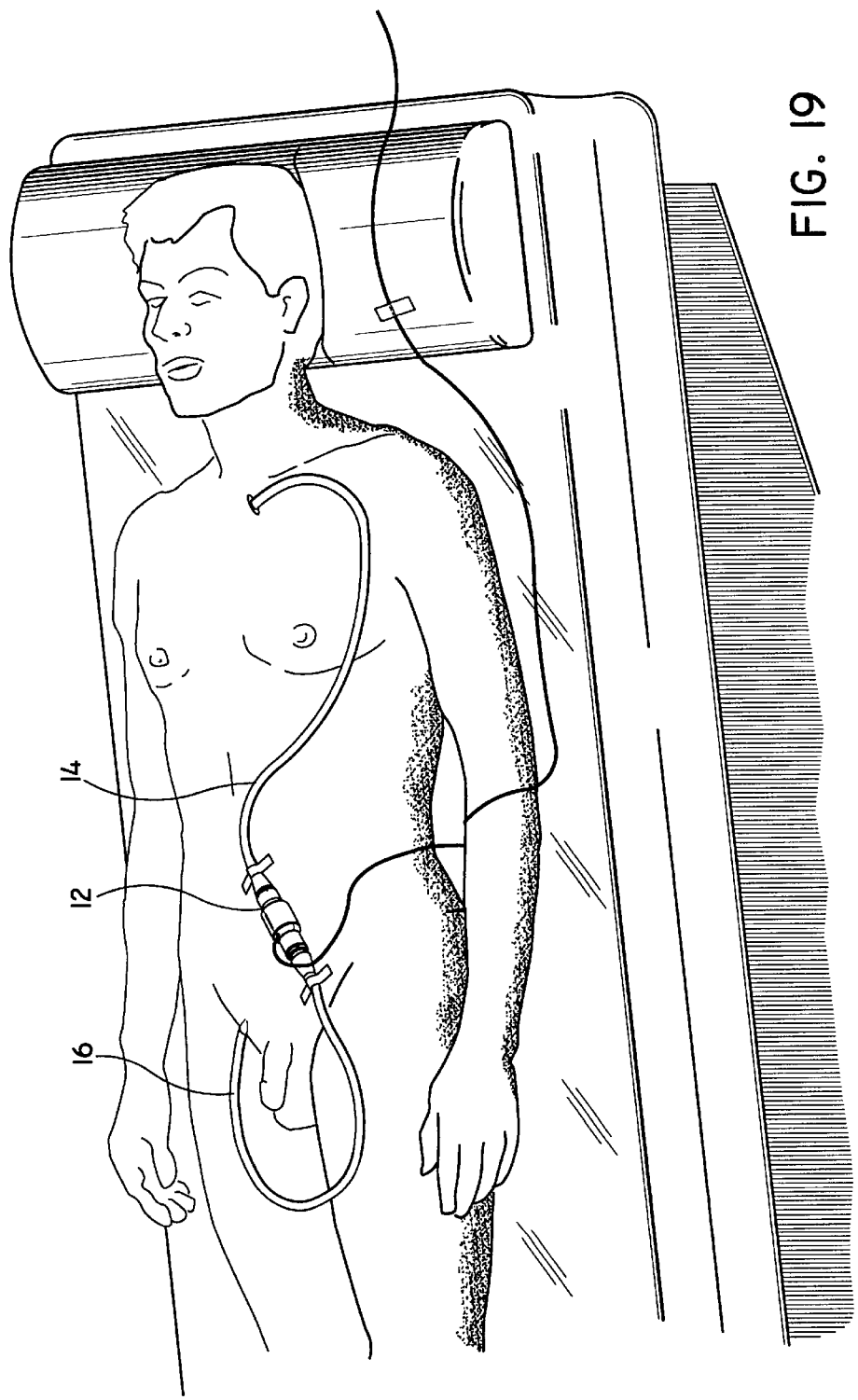
FIGS. 19–20 are views illustrating an alternative percutaneous method of application where the inlet cannula accesses the left ventricle through the aortic valve and the outlet cannula accesses the descending aorta through the femoral artery.
Figure 20:
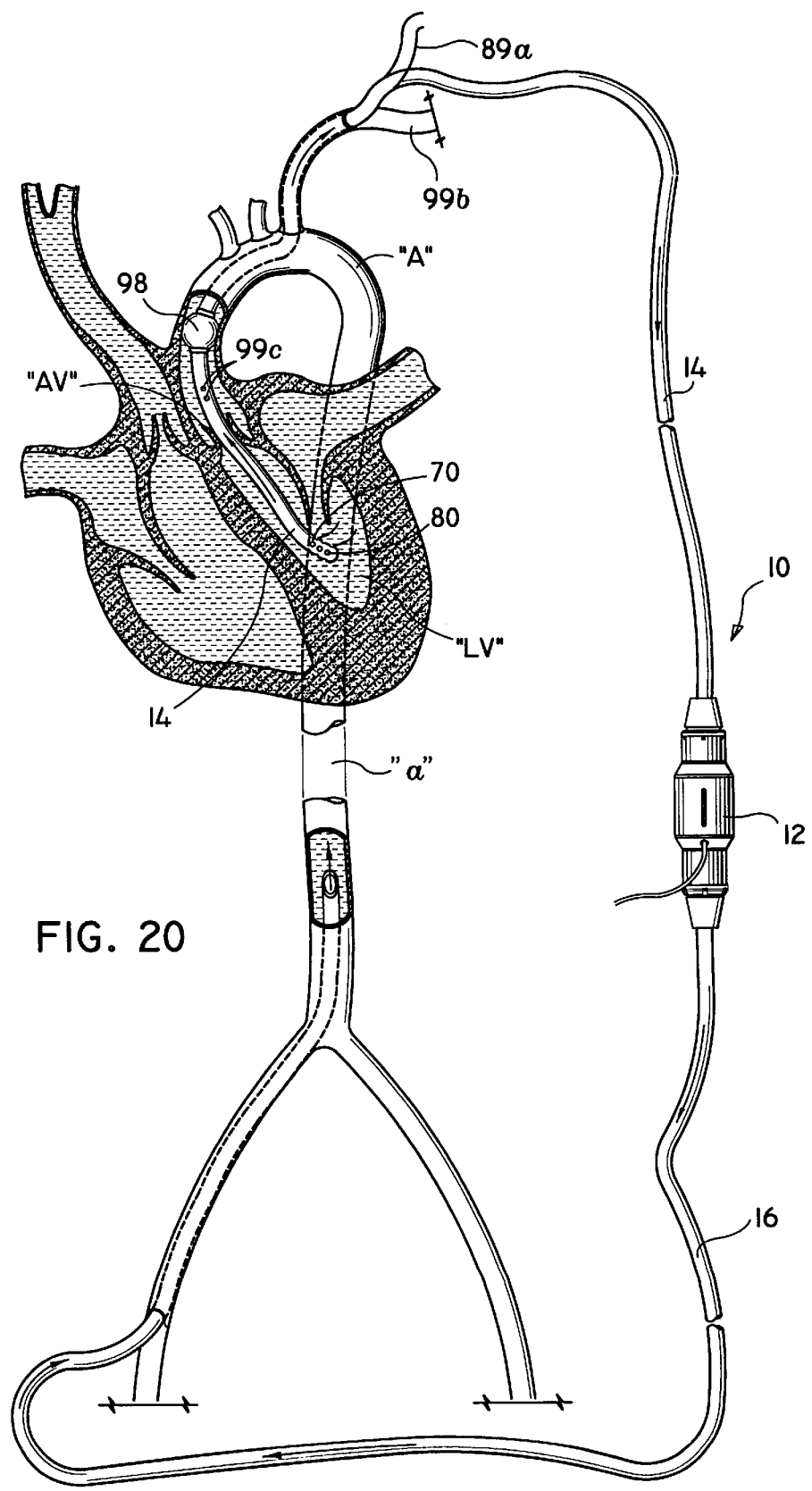

FIGS. 19–20 illustrate yet another method of application of the circulatory support system. In accordance with this percutaneous approach, inflow cannula 70 is percutaneously inserted through subclavian artery to the aorta "A" and advanced through the aortic valve "AV" with the inflow ports 80 of the tube 14 positioned within the left ventricle "LV". Inflow cannula 70 has expandable membrane 98 (e.g., a balloon) positioned about its periphery to occlude the aorta "A". A second catheter 99 (as shown) may be coaxially mounted about the cannula 70 to provide the inflation fluids to expand membrane 98 as is conventional in the art. The second catheter may include a connector 99a, e.g., a Luer connector, for providing the inflation fluids to be passed to membrane 98. It is also envisioned that inflow catheter 14 may have a separate lumen extending therethrough and terminating in a port 99b and port 99c to permit the introduction of cardioplegia solution within the heart to temporarily discontinue the pumping function of the heart, and/or for venting the left ventricle. Outflow cannula 70 is inserted, preferably, percutaneously within the femoral artery and advanced into the descending aorta "a".

In application, flexible membrane 98 is expanded to isolate the left side of the heart. The support system 10 is actuated to draw blood from the left ventricle "LV" through inflow ports 80 and into inflow cannula 70. The blood is directed through inflow cannula 70 and is subjected to the pumping energy of portable pump 12. The blood is returned through tube 68 and outflow cannula 72 and into the descending aorta "a". During use, cardioplegia fluid or venting capabilities may be introduced via inflow catheter tube 14 and port 99b to be deposited from port 99c as described above.

Figure 21:
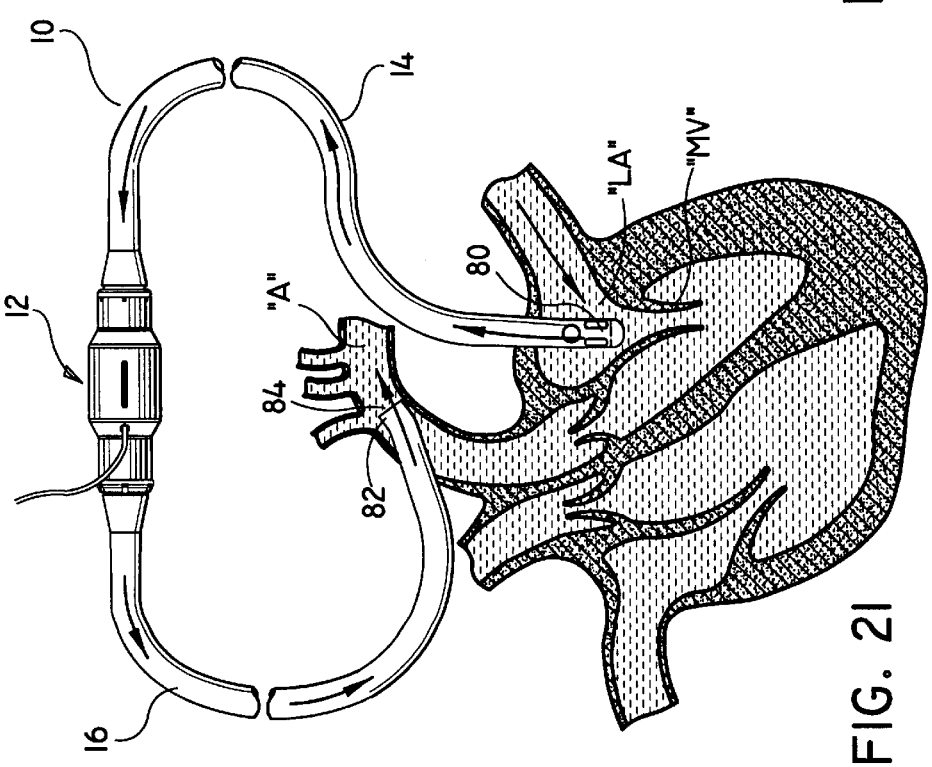
FIG. 21 is a view illustrating another method of application of the circulatory support system where the inlet cannulated tube accesses the left atrium of the heart and the outlet cannulated tube is disposed in the aorta.

With reference now to FIG. 21, another arrangement for connecting the system is described. Inlet cannulated tube 14 is introduced through the heart wall with the inflow ports 80 positioned in the left atrium "LA" as shown. Outlet cannula 72 is inserted through the aorta wall with the use of end portion 82 with the outflow port 84 positioned in a downstream position within the aorta "A". Upon operation of the system 10, blood is withdrawn from the left atrium "LA" through inflow ports 80 of inflow cannula 70 and directed to the pump 12. Pump 12 imparts mechanical pumping energy to the blood and directs the blood under pressure through outflow cannula 72 and into the aorta "A", thus assisting the functioning of the left side of the heart. The blood is circulated throughout the body via the body's circulatory system through the right side of the heart to the patient's lungs for oxygenation.

Figure 22:
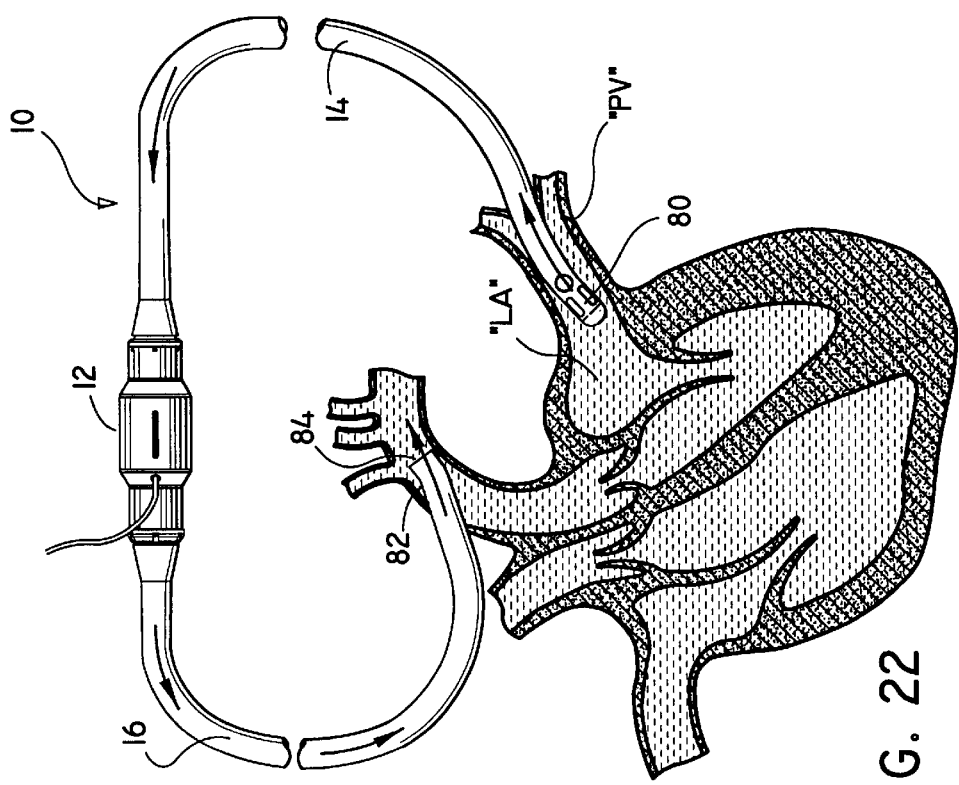
FIG. 22 is a view illustrating another method of application of the circulatory support system where the inlet cannulated tube accesses the left atrium through the juncture of the pulmonary veins.

FIG. 22 illustrates another alternate method of application of circulatory support system 10. In accordance with this method of application, inflow cannula 70 is introduced into the left atrium "LA" through the region of the juncture of the pulmonary veins "PV" with the inflow ports 80 of the cannula 70 located within the left atrium "LA".

Figure 23:
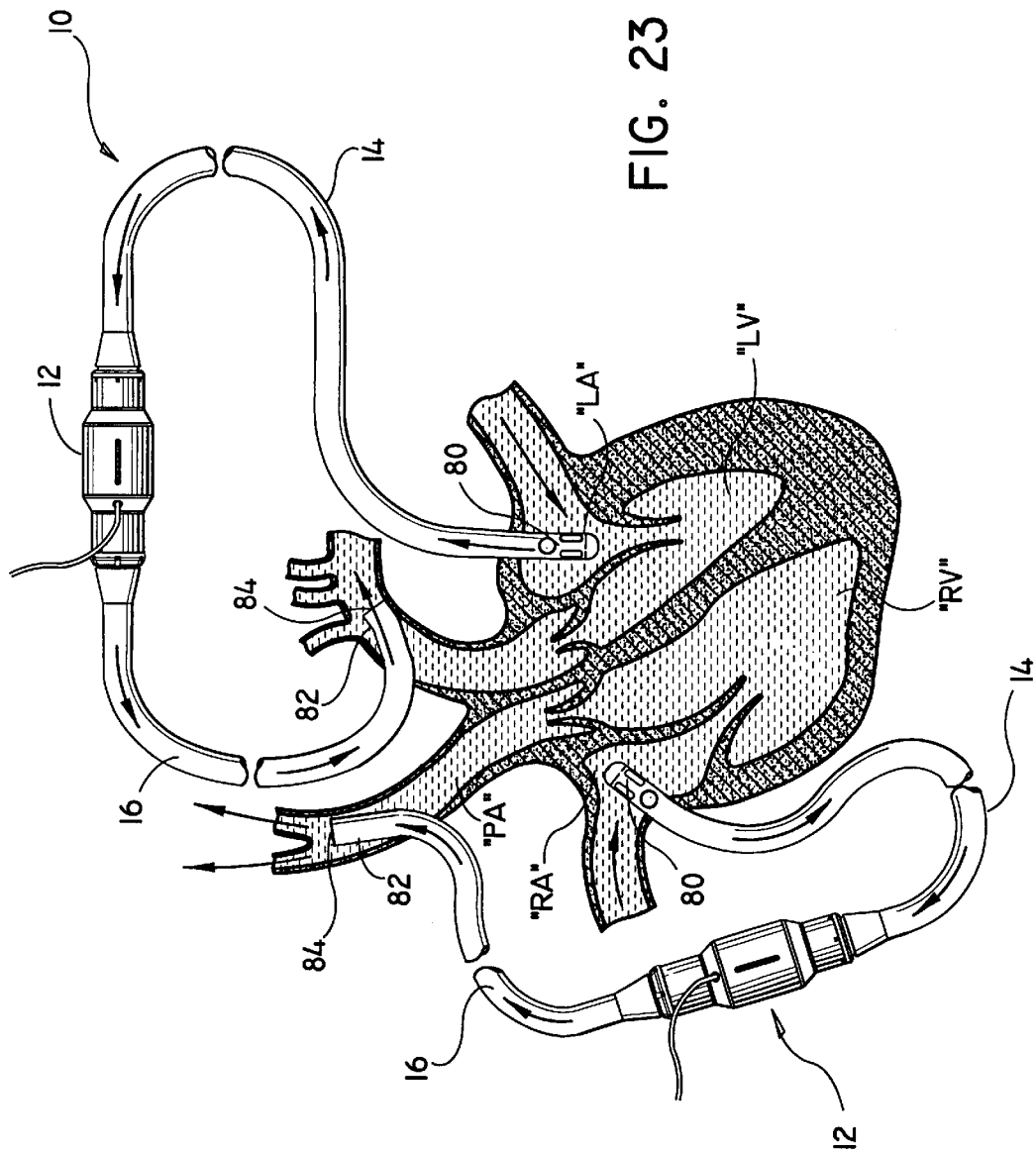
FIG. 23 is a view illustrating the use of a second circulatory support system for assisting the right side of the heart.

FIG. 23 illustrates an alternate method of application where two support systems are used for total heart bypass. The support system utilized for bypass of the left side of the heart is identical to that described in connection with FIG. 21. The support system utilized for right heart bypass has its inflow cannula 70 inserted through the heart wall with the inflow ports 80 positioned in the right atrium "RA". The outflow cannula 72 is positioned in the pulmonary aorta "PA" in downstream orientation as shown. In this application, the lungs are still utilized to oxygenate the blood. Alternatively, right bypass can be effectuated by accessing the right ventricle with inflow cannula 70 or left bypass can be effectuated by accessing the left ventricle with any of the arrangements described above.

Thus, the circulatory support system 10 of the present disclosure provides for temporary short term heart support (either partial, e.g., left heart assist, or full support) of a patient. Set-up and management of the system requires relatively minimal effort. The entire system 10, i.e., the pump 12 including the motor 60 and associated tubing, can be manufactured cost effectively to be disposable. The features of the control unit, including the bubble detection, flow rate detection, automatic motor shutdown and clamping of the outlet cannula in case of detected bubble, various visible and audible alarms, and so forth, are particularly tailored to address the needs of an axial flow pump system. The control unit is also ergonomically designed to occupy a small amount of operating room space and to facilitate use in the operating room.

While the above description contains many specifics, these specifics should not be construed as limitations on the scope of the disclosure, but merely as exemplifications of preferred embodiments thereof. For example, one or two of the aforedescribed pumps can be placed in other locations of the body, via other access areas, in addition to those described above. Also, the pump(s) can be utilized during the "window" approach to bypass surgery as well as during minimally invasive bypass surgery. Those skilled in the art will envision many other possible variations that are within the scope and spirit of the disclosure as defined by the claims appended hereto.

What is claimed is:

1. A circulatory support system to supplement or temporarily replace the pumping function of a patient's heart to hereby enable a surgeon to perform surgical procedures thereon, comprising:

an extracorporeal portable blood flow pump including a pump housing having inlet and outlet ports, a pump member mounted in the pump housing to impart mechanical energy to blood entering the inlet port and to direct the blood through the outlet port, the pump member having a variable output;

an inlet cannula connected to the inlet port of the pump housing and having an inlet open end portion defining an ingress path such that when it is inserted within the patient's heart or blood vessel associated with the heart, blood is drawn from the patient through the inlet open end portion of the inlet cannula and directed into the pump housing;

an outlet cannula connected to the outlet port of the pump housing and having a lumen and an outlet end portion for insertion within the patient so that blood exiting the outlet port of the pump housing is conveyed through the lumen of the outlet cannula into the patient for transfer by the arterial system of the patient;

a control unit having a processor, operatively coupled to the flow pump, for controlling operation thereof; and a pressure transducer mounted to a distal end of the inlet cannula for insertion into and sensing pressure within the patient's heart or blood vessel associated with the heart and providing a pressure sense signal indicative of the pressure sensed to the control unit, the control unit being operable to command a reduction in the output of the pump member when the pressure is determined to be below a predetermined threshold.

2. The system of claim 1 wherein said pressure transducer is disposed in proximity to the inlet open end portion of the inlet cannula, and the system further including a wire running within an outer sheathing of the inlet cannula from the control unit to the pressure transducer, the pressure sense signal being transmitted to the control unit on the wire.

3. The system of claim 1 wherein the reduction in motor speed to a lower speed is repeated such that the motor speed is ramped down, until the pressure is determined to have risen to a value above a predefined threshold, and the control unit being operative to ramp up the motor speed if the pressure has risen above the predefined threshold.

4. The system of claim 1, further including an air bubble sensor mounted to one of the cannulas for detecting air bubbles in the respective cannula and providing a bubble detect signal indicative of the presence of an air bubble;

wherein the control unit is operative, responsive to receiving a bubble detect signal, to generate an air bubble alarm and to cause the pump member to cease operation thereof.

5. The system of claim 1 wherein said blood flow pump comprises an axial blood flow pump.

6. The system of claim 1, wherein the pressure transducer is mounted to the inlet open end portion of the inlet cannula.

7. A circulatory support system to supplement or temporarily replace the pumping function of a heart, which comprises:

a blood flow pump having blood inflow and outflow openings and being adapted to impart pump energy to blood directed thereto, the blood pump having a varying output;

an inlet cannula in fluid communication with the blood inflow opening of the pump, the inlet cannula having an inlet open end portion defining an ingress path such that when the inlet open end portion is inserted within a patient's body it percutaneously accesses at least one of a vessel and heart of a patient, draws blood from within the at least one of the vessel and heart and directs the blood to the blood pump;

an outlet cannula in fluid communication with the blood outflow opening of the pump, the outlet cannula being dimensioned and configured for percutaneously accessing a vessel of the patient to return blood from the pump to the vessel accessed thereby;

a pressure transducer mounted to the inlet cannula proximal of the inlet open end portion for insertion into and sensing pressure within the one of the vessel and heart of the patient for monitoring pressure therein;

a control unit including a processor operatively coupled to the blood pump for controlling operation of the blood pump, the control unit including:

circuitry for supplying power to the blood pump to activate the pump; and circuitry associated with the pressure transducer, and being responsive to a signal from the pressure transducer to command a reduction in the output of the blood pump when the pressure is determined to be below a predetermined minimum value.

8. The circulatory support system of claim 7 wherein the circuitry associated with the pressure transducer is adapted to reduce the output of the blood pump at a predetermined rate of reduction when the pressure is determined to be below the predetermined minimum value whereby, when the pressure is determined to have risen to at least the predetermined minimum value, the output of the pump is increased to a desired value thereof.

9. The circulatory support system of claim 8 wherein the output of the pump is increased to the desired value thereof subsequent to maintaining the predetermined minimum value of the pressure for a predetermined period of time.

10. The circulatory support system of claim 9 including an air bubble sensor mounted to one of the cannulas for detecting air bubbles and providing a bubble detect signal indicative of the presence of an air bubble.

11. The circulatory support system of claim 10 including a clamping device mounted to one of the cannulas and operative to clamp the respective cannula in response to the bubble detect signal to prevent air from entering the patient's bloodstream.

* * * * *